US011599672B2

(12) United States Patent
Stalling et al.

(10) Patent No.: US 11,599,672 B2
(45) Date of Patent: Mar. 7, 2023

(54) METHOD AND APPARATUS FOR ANONYMIZED DISPLAY AND DATA EXPORT

(71) Applicant: PME IP PTY LTD, Richmond (AU)

(72) Inventors: Detlev Stalling, Berlin (DE); Malte Westerhoff, Berlin (DE)

(73) Assignee: PME IP PTY LTD, Richmond (AU)

( * ) Notice: Subject to any disclaimer, the term of this patent is extended or adjusted under 35 U.S.C. 154(b) by 709 days.

(21) Appl. No.: 15/218,993

(22) Filed: Jul. 25, 2016

(65) Prior Publication Data

US 2017/0032084 A1 Feb. 2, 2017

Related U.S. Application Data

(60) Provisional application No. 62/199,630, filed on Jul. 31, 2015.

(51) Int. Cl.
*G06F 21/62* (2013.01)
*G16H 10/60* (2018.01)
*G16H 30/40* (2018.01)

(52) U.S. Cl.
CPC ......... *G06F 21/6254* (2013.01); *G16H 10/60* (2018.01); *G16H 30/40* (2018.01)

(58) Field of Classification Search
CPC ...... G06F 19/321; G16H 10/60; G16H 30/40; G96F 21/6254
USPC .......................................................... 705/2
See application file for complete search history.

(56) References Cited

U.S. PATENT DOCUMENTS

| | | |
|---|---|---|
| 2,658,310 A | 11/1953 | Cook |
| 3,431,200 A | 3/1969 | Davis et al. |
| 3,645,040 A | 2/1972 | Ort |
| 4,137,868 A | 2/1979 | Pryor |
| 4,235,043 A | 11/1980 | Harasawa et al. |
| 4,258,661 A | 3/1981 | Margen |
| 4,267,038 A | 5/1981 | Thompson |

(Continued)

FOREIGN PATENT DOCUMENTS

| | | |
|---|---|---|
| DE | 10317384 | 4/2004 |
| EP | 0492897 | 7/1992 |

(Continued)

OTHER PUBLICATIONS

Required DICOM Information Standards, [online], last posting date, Feb. 10, 2015, available at: < https://siim.org/forums/Posts.aspx?topic=1068396&page=1 > (Year: 2015).*

(Continued)

*Primary Examiner* — Richard W. Crandall
(74) *Attorney, Agent, or Firm* — Sci-Law Strategies, PC

(57) ABSTRACT

In an embodiment of the present invention, users with the appropriate permission can launch a function inside a system in order to anonymize and export the currently loaded study or studies, or one or more studies identified by a search criteria. The data from the studies that were identified is then anonymized on the system. In an embodiment of the present invention, the data from selected studies is anonymized on a server, and only then transmitted to another network device. In an alternative embodiment of the present invention, the data from selected studies is anonymized on a server, and only then stored to a hard disk or other media.

18 Claims, 10 Drawing Sheets

(56) References Cited

U.S. PATENT DOCUMENTS

| | | |
|---|---|---|
| 4,320,594 A | 3/1982 | Raymond |
| 4,746,795 A | 5/1988 | Stewart et al. |
| 4,905,148 A | 2/1990 | Crawford |
| 4,910,912 A | 3/1990 | Lowrey, III |
| 4,928,250 A | 5/1990 | Greenberg et al. |
| 4,958,460 A | 9/1990 | Nielson et al. |
| 4,984,160 A | 1/1991 | Saint Felix et al. |
| 5,031,117 A | 7/1991 | Minor et al. |
| 5,091,960 A | 2/1992 | Butler |
| 5,121,708 A | 6/1992 | Nuttle |
| 5,128,864 A | 7/1992 | Waggener et al. |
| 5,218,534 A | 6/1993 | Trousset et al. |
| 5,235,510 A | 8/1993 | Yamada |
| 5,241,471 A | 8/1993 | Trousset et al. |
| 5,253,171 A | 10/1993 | Hsiao et al. |
| 5,274,759 A | 12/1993 | Yoshioka |
| 5,280,428 A | 1/1994 | Wu et al. |
| 5,287,274 A | 2/1994 | Saint Felix et al. |
| 5,293,313 A | 3/1994 | Cecil |
| 5,307,264 A | 4/1994 | Waggener et al. |
| 5,355,453 A | 10/1994 | Row et al. |
| 5,368,033 A | 11/1994 | Moshfeghi |
| 5,375,156 A | 12/1994 | Kuo-Petravic et al. |
| 5,412,703 A | 5/1995 | Goodenough et al. |
| 5,412,764 A | 5/1995 | Tanaka |
| 5,442,672 A | 8/1995 | Bjorkholm et al. |
| 5,452,416 A | 9/1995 | Hilton |
| 5,488,700 A | 1/1996 | Glassner |
| 5,560,360 A | 10/1996 | Filler |
| 5,594,842 A | 1/1997 | Kaufman et al. |
| 5,602,892 A | 2/1997 | Llacer |
| 5,633,951 A | 5/1997 | Moshfeghi |
| 5,633,999 A | 5/1997 | Clowes et al. |
| 5,640,436 A | 6/1997 | Kawai et al. |
| 5,671,265 A | 9/1997 | Andress |
| 5,744,802 A | 4/1998 | Muehllehner et al. |
| 5,774,519 A | 6/1998 | Lindstrom et al. |
| 5,790,787 A | 8/1998 | Scott et al. |
| 5,793,374 A | 8/1998 | Guenter et al. |
| 5,793,879 A | 8/1998 | Benn et al. |
| 5,813,988 A | 9/1998 | Alfano et al. |
| 5,821,541 A | 10/1998 | Tumer |
| 5,825,842 A | 10/1998 | Taguchi |
| 5,838,756 A | 11/1998 | Taguchi et al. |
| 5,841,140 A | 11/1998 | McCroskey et al. |
| 5,909,476 A | 6/1999 | Cheng et al. |
| 5,930,384 A | 7/1999 | Guillemaud et al. |
| 5,931,789 A | 8/1999 | Alfano et al. |
| 5,950,203 A | 9/1999 | Stakuis |
| 5,960,056 A | 9/1999 | Lai |
| 5,963,612 A | 10/1999 | Navab |
| 5,963,613 A | 10/1999 | Navab |
| 5,963,658 A | 10/1999 | Klibanov et al. |
| 6,002,739 A | 12/1999 | Heumann |
| 6,018,562 A | 1/2000 | Willson |
| 6,032,264 A | 2/2000 | Beffa et al. |
| 6,044,132 A | 3/2000 | Navab |
| 6,049,390 A | 4/2000 | Notredame |
| 6,049,582 A | 4/2000 | Navab |
| 6,072,177 A | 6/2000 | Mccroskey et al. |
| 6,088,423 A | 7/2000 | Krug et al. |
| 6,091,422 A | 7/2000 | Ouaknine et al. |
| 6,104,827 A | 8/2000 | Benn et al. |
| 6,105,029 A | 8/2000 | Maddalozzo, Jr. et al. |
| 6,108,007 A | 8/2000 | Shochet |
| 6,108,576 A | 8/2000 | Alfano et al. |
| 6,123,733 A | 9/2000 | Dalton |
| 6,175,655 B1 | 1/2001 | George |
| 6,205,120 B1 | 3/2001 | Packer et al. |
| 6,219,061 B1 | 4/2001 | Lauer et al. |
| 6,226,005 B1 | 5/2001 | Laferriere |
| 6,236,704 B1 | 5/2001 | Navab et al. |
| 6,243,098 B1 | 6/2001 | Lauer et al. |
| 6,249,594 B1 | 6/2001 | Hibbard |
| 6,255,655 B1 | 7/2001 | McCroskey et al. |
| 6,264,610 B1 | 7/2001 | Zhu |
| 6,268,846 B1 | 7/2001 | Georgiev |
| 6,278,460 B1 | 8/2001 | Myers et al. |
| 6,282,256 B1 | 8/2001 | Grass et al. |
| 6,289,235 B1 | 9/2001 | Webber et al. |
| 6,304,771 B1 | 10/2001 | Yodh et al. |
| 6,320,928 B1 | 11/2001 | Vaillant et al. |
| 6,324,241 B1 | 11/2001 | Besson |
| 6,377,257 B1 | 4/2002 | Borrel |
| 6,377,266 B1 | 4/2002 | Baldwin |
| 6,384,821 B1 | 5/2002 | Borrel |
| 6,404,843 B1 | 6/2002 | Vaillant |
| 6,415,013 B1 | 7/2002 | Hsieh et al. |
| 6,470,067 B1 | 10/2002 | Harding |
| 6,470,070 B2 | 10/2002 | Menhardt |
| 6,473,793 B1 | 10/2002 | Dillon et al. |
| 6,475,150 B2 | 11/2002 | Haddad |
| 6,507,633 B1 | 1/2003 | Elbakri et al. |
| 6,510,241 B1 | 1/2003 | Vaillant et al. |
| 6,519,355 B2 | 2/2003 | Nelson |
| 6,526,305 B1 | 2/2003 | Mori |
| 6,557,102 B1 * | 4/2003 | Wong ..................... G06F 21/00 |
| | | 713/176 |
| 6,559,958 B2 | 5/2003 | Motamed |
| 6,591,004 B1 | 7/2003 | VanEssen et al. |
| 6,615,063 B1 | 9/2003 | Ntziachristos et al. |
| 6,633,688 B1 | 10/2003 | Nixon |
| 6,636,623 B2 | 10/2003 | Nelson et al. |
| 6,654,012 B1 | 11/2003 | Lauer et al. |
| 6,658,142 B1 | 12/2003 | Kam et al. |
| 6,664,963 B1 | 12/2003 | Zatz |
| 6,674,430 B1 | 1/2004 | Kaufman et al. |
| 6,697,508 B2 | 2/2004 | Nelson |
| 6,707,878 B2 | 3/2004 | Claus et al. |
| 6,718,195 B2 | 4/2004 | Van Der Mark et al. |
| 6,731,283 B1 | 5/2004 | Navab |
| 6,740,232 B1 | 5/2004 | Beaulieu |
| 6,741,730 B2 | 5/2004 | Rahn et al. |
| 6,744,253 B2 | 6/2004 | Stolarczyk |
| 6,744,845 B2 | 6/2004 | Harding et al. |
| 6,745,070 B2 | 6/2004 | Wexler et al. |
| 6,747,654 B1 | 6/2004 | Laksono et al. |
| 6,754,299 B2 | 6/2004 | Patch |
| 6,765,981 B2 | 7/2004 | Heumann |
| 6,768,782 B1 | 7/2004 | Hsieh et al. |
| 6,770,893 B2 | 8/2004 | Nelson |
| 6,771,733 B2 | 8/2004 | Katsevich |
| 6,778,127 B2 | 8/2004 | Stolarczyk et al. |
| 6,785,409 B1 | 8/2004 | Suri |
| 6,798,417 B1 | 9/2004 | Taylor |
| 6,807,581 B1 | 10/2004 | Starr et al. |
| 6,825,840 B2 | 11/2004 | Gritz |
| 6,825,843 B2 | 11/2004 | Allen et al. |
| 6,923,906 B2 | 8/2005 | Oswald et al. |
| 6,947,047 B1 | 9/2005 | Moy et al. |
| 6,978,206 B1 | 12/2005 | Pu |
| 7,003,547 B1 | 2/2006 | Hubbard |
| 7,006,101 B1 | 2/2006 | Brown et al. |
| 7,031,022 B1 | 4/2006 | Komori et al. |
| 7,034,828 B1 | 4/2006 | Drebin et al. |
| 7,039,723 B2 | 5/2006 | Hu |
| 7,050,953 B2 | 5/2006 | Chiang et al. |
| 7,054,852 B1 | 5/2006 | Cohen |
| 7,058,644 B2 | 6/2006 | Patchet et al. |
| 7,076,735 B2 | 7/2006 | Callegari |
| 7,098,907 B2 | 8/2006 | Houston et al. |
| 7,120,283 B2 | 10/2006 | Thieret |
| 7,133,041 B2 | 11/2006 | Kaufman et al. |
| 7,154,985 B2 | 12/2006 | Dobbs |
| 7,167,176 B2 | 1/2007 | Sloan et al. |
| 7,184,041 B2 | 2/2007 | Heng et al. |
| 7,185,003 B2 | 2/2007 | Bayliss et al. |
| 7,219,085 B2 | 5/2007 | Buck et al. |
| 7,242,401 B2 | 7/2007 | Yang et al. |
| 7,262,770 B2 | 8/2007 | Sloan et al. |
| 7,274,368 B1 | 9/2007 | Keslin |
| 7,299,232 B2 | 11/2007 | Stakutis et al. |
| 7,315,926 B2 | 1/2008 | Fridella et al. |
| 7,324,116 B2 | 1/2008 | Boyd et al. |

(56) References Cited

U.S. PATENT DOCUMENTS

| | | |
|---|---|---|
| 7,339,585 B2 | 3/2008 | Verstraelen et al. |
| 7,472,156 B2 | 12/2008 | Philbrick et al. |
| 7,502,869 B2 | 3/2009 | Boucher et al. |
| 7,506,375 B2 | 3/2009 | Kanda et al. |
| 7,552,192 B2 | 6/2009 | Carmichael |
| 7,609,884 B1 | 10/2009 | Stalling |
| 7,693,318 B1 | 4/2010 | Stalling |
| 7,701,210 B2 | 4/2010 | Ichinose |
| 7,778,392 B1 | 8/2010 | Bergman |
| 7,876,944 B2 | 1/2011 | Stalling |
| 7,889,895 B2 | 2/2011 | Nowinski |
| 7,899,516 B2 | 3/2011 | Chen et al. |
| 7,907,759 B2 | 3/2011 | Hundley |
| 7,956,612 B2 | 6/2011 | Sorensen |
| 7,983,300 B2 | 7/2011 | Vaughan et al. |
| 7,991,837 B1 | 8/2011 | Tahan |
| 7,995,824 B2 | 8/2011 | Yim |
| 8,107,592 B2 | 1/2012 | Bergman |
| 8,189,002 B1 | 5/2012 | Westerhoff |
| 8,319,781 B2 | 11/2012 | Westerhoff |
| 8,369,600 B2 | 2/2013 | Can et al. |
| 8,386,560 B2 | 2/2013 | Ma |
| 8,392,529 B2 | 3/2013 | Westerhoff |
| 8,508,539 B2 | 8/2013 | Vlietinck |
| 8,538,108 B2 | 9/2013 | Shekhar |
| 8,542,136 B1 | 9/2013 | Owsley et al. |
| 8,548,215 B2 | 10/2013 | Westerhoff |
| 8,775,510 B2 | 7/2014 | Westerhoff |
| 8,976,190 B1 | 3/2015 | Westerhoff |
| 9,019,287 B2 | 4/2015 | Westerhoff |
| 9,167,027 B2 | 10/2015 | Westerhoff |
| 9,299,156 B2 | 3/2016 | Zalis |
| 9,355,616 B2 | 5/2016 | Westerhoff |
| 9,454,813 B2 | 9/2016 | Westerhoff |
| 9,509,802 B1 | 11/2016 | Westerhoff |
| 9,524,577 B1 | 12/2016 | Westerhoff |
| 9,595,242 B1 | 3/2017 | Westerhoff |
| 9,728,165 B1 | 8/2017 | Westerhoff |
| 9,749,245 B2 | 8/2017 | Stalling |
| 9,860,300 B2 | 1/2018 | Westerhoff |
| 9,898,855 B2 | 2/2018 | Westerhoff |
| 9,904,969 B1 | 2/2018 | Westerhoff |
| 9,984,460 B2 | 5/2018 | Westerhoff |
| 9,984,478 B2 | 5/2018 | Westerhoff |
| 10,070,839 B2 | 9/2018 | Westerhoff |
| 10,311,541 B2 | 6/2019 | Westerhoff |
| 10,320,684 B2 | 6/2019 | Stalling |
| 10,373,368 B2 | 8/2019 | Westerhoff |
| 10,380,970 B2 | 8/2019 | Westerhoff |
| 10,430,914 B2 | 10/2019 | Westerhoff |
| 11,183,292 B2 * | 11/2021 | Stalling .............. G16H 15/00 |
| 2001/0026848 A1 | 10/2001 | Van Der Mark |
| 2002/0016813 A1 | 2/2002 | Woods et al. |
| 2002/0034817 A1 | 3/2002 | Henry et al. |
| 2002/0049825 A1 | 4/2002 | Jewett et al. |
| 2002/0080143 A1 | 6/2002 | Morgan et al. |
| 2002/0089587 A1 | 7/2002 | White et al. |
| 2002/0099290 A1 | 7/2002 | Haddad |
| 2002/0099844 A1 | 7/2002 | Baumann et al. |
| 2002/0120727 A1 | 8/2002 | Curley et al. |
| 2002/0123680 A1 | 9/2002 | Vailant |
| 2002/0138019 A1 | 9/2002 | Wexler |
| 2002/0150202 A1 | 10/2002 | Harding |
| 2002/0150285 A1 | 10/2002 | Nelson |
| 2002/0180747 A1 | 12/2002 | Lavelle et al. |
| 2002/0184238 A1 | 12/2002 | Chylla |
| 2002/0184349 A1 | 12/2002 | Maukyan |
| 2003/0001842 A1 | 1/2003 | Munshi |
| 2003/0031352 A1 | 2/2003 | Nelson et al. |
| 2003/0059110 A1 | 3/2003 | Wilt |
| 2003/0065268 A1 | 4/2003 | Chen et al. |
| 2003/0086599 A1 | 5/2003 | Armato |
| 2003/0103666 A1 | 6/2003 | Edie et al. |
| 2003/0120743 A1 | 6/2003 | Coatney et al. |
| 2003/0123720 A1 | 7/2003 | Launay et al. |
| 2003/0149812 A1 | 8/2003 | Schoenthal et al. |
| 2003/0158786 A1 | 8/2003 | Yaron |
| 2003/0176780 A1 | 9/2003 | Arnold |
| 2003/0179197 A1 | 9/2003 | Sloan et al. |
| 2003/0194049 A1 | 10/2003 | Claus et al. |
| 2003/0220569 A1 | 11/2003 | Dione |
| 2003/0220772 A1 | 11/2003 | Chiang et al. |
| 2003/0227456 A1 | 12/2003 | Gritz |
| 2003/0234791 A1 | 12/2003 | Boyd et al. |
| 2004/0010397 A1 | 1/2004 | Barbour et al. |
| 2004/0012596 A1 | 1/2004 | Allen et al. |
| 2004/0015062 A1 | 1/2004 | Ntziachristos et al. |
| 2004/0022348 A1 | 2/2004 | Heumann |
| 2004/0059822 A1 | 3/2004 | Jiang |
| 2004/0066384 A1 | 4/2004 | Ohba |
| 2004/0066385 A1 | 4/2004 | Kilgard |
| 2004/0066891 A1 | 4/2004 | Freytag |
| 2004/0078238 A1 * | 4/2004 | Thomas ............... G06F 19/321 705/3 |
| 2004/0102688 A1 | 5/2004 | Walker |
| 2004/0125103 A1 | 7/2004 | Kaufman |
| 2004/0133652 A1 | 7/2004 | Miloushev et al. |
| 2004/0147039 A1 | 7/2004 | Van Der Mark |
| 2004/0162677 A1 | 8/2004 | Bednar |
| 2004/0170302 A1 | 9/2004 | Museth et al. |
| 2004/0193901 A1 * | 9/2004 | Bharara ............... G16H 10/60 713/193 |
| 2004/0210584 A1 | 10/2004 | Nir et al. |
| 2004/0215858 A1 | 10/2004 | Armstrong et al. |
| 2004/0215868 A1 | 10/2004 | Solomon et al. |
| 2004/0239672 A1 | 12/2004 | Schmidt |
| 2004/0240753 A1 | 12/2004 | Hu |
| 2005/0012753 A1 | 1/2005 | Karlov |
| 2005/0017972 A1 | 1/2005 | Poole et al. |
| 2005/0066095 A1 | 3/2005 | Mullick et al. |
| 2005/0088440 A1 | 4/2005 | Sloan et al. |
| 2005/0128195 A1 | 6/2005 | Houston et al. |
| 2005/0152590 A1 | 7/2005 | Thieret |
| 2005/0165623 A1 * | 7/2005 | Landi ................. G06F 21/6254 705/2 |
| 2005/0225554 A1 | 10/2005 | Bastos et al. |
| 2005/0231503 A1 | 10/2005 | Heng et al. |
| 2005/0239182 A1 | 10/2005 | Berzin |
| 2005/0240628 A1 | 10/2005 | Jiang et al. |
| 2005/0256742 A1 * | 11/2005 | Kohan ................. G06F 21/6245 705/2 |
| 2005/0259103 A1 | 11/2005 | Kilgard et al. |
| 2005/0270298 A1 | 12/2005 | Thieret |
| 2005/0271302 A1 | 12/2005 | Khamene et al. |
| 2006/0010438 A1 | 1/2006 | Brady et al. |
| 2006/0010454 A1 | 1/2006 | Napoli et al. |
| 2006/0028479 A1 | 2/2006 | Chun |
| 2006/0034511 A1 | 2/2006 | Verstraelen |
| 2006/0066609 A1 | 3/2006 | Iodice |
| 2006/0214949 A1 | 8/2006 | Zhang |
| 2006/0197780 A1 | 9/2006 | Watkins et al. |
| 2006/0239540 A1 | 10/2006 | Serra |
| 2006/0239589 A1 | 10/2006 | Omernick |
| 2006/0282253 A1 | 12/2006 | Buswell et al. |
| 2007/0005798 A1 * | 1/2007 | Gropper ............... G06F 19/321 709/238 |
| 2007/0038939 A1 | 2/2007 | Challen |
| 2007/0046966 A1 | 3/2007 | Mussack |
| 2007/0067497 A1 | 3/2007 | Craft et al. |
| 2007/0092864 A1 | 4/2007 | Reinhardt |
| 2007/0097133 A1 | 5/2007 | Stauffer et al. |
| 2007/0116332 A1 | 5/2007 | Cai et al. |
| 2007/0127802 A1 | 6/2007 | Odry |
| 2007/0156955 A1 | 7/2007 | Royer, Jr. |
| 2007/0165917 A1 | 7/2007 | Cao et al. |
| 2007/0185879 A1 | 8/2007 | Roublev et al. |
| 2007/0188488 A1 | 8/2007 | Choi |
| 2007/0226314 A1 | 9/2007 | Eick et al. |
| 2007/0280518 A1 | 12/2007 | Nowinski |
| 2008/0009055 A1 | 1/2008 | Lewnard |
| 2008/0042923 A1 | 2/2008 | De Laet |
| 2008/0086557 A1 | 4/2008 | Roach |
| 2008/0115139 A1 | 5/2008 | Inglett et al. |
| 2008/0137929 A1 | 6/2008 | Chen et al. |

(56) References Cited

U.S. PATENT DOCUMENTS

| | | | |
|---|---|---|---|
| 2008/0147554 A1* | 6/2008 | Stevens | G06F 21/6254 |
| | | | 705/51 |
| 2008/0155890 A1 | 7/2008 | Oyler | |
| 2008/0174593 A1 | 7/2008 | Ham | |
| 2008/0208961 A1 | 8/2008 | Kim et al. | |
| 2008/0224700 A1 | 9/2008 | Sorensen | |
| 2008/0281908 A1 | 11/2008 | McCanne et al. | |
| 2008/0317317 A1 | 12/2008 | Shekhar | |
| 2009/0005693 A1 | 1/2009 | Brauner et al. | |
| 2009/0043988 A1 | 2/2009 | Archer et al. | |
| 2009/0077097 A1 | 3/2009 | Lacapra et al. | |
| 2009/0147793 A1 | 6/2009 | Hayakawa et al. | |
| 2009/0208082 A1 | 8/2009 | Westerhoff et al. | |
| 2009/0210487 A1 | 8/2009 | Westerhoff et al. | |
| 2009/0225076 A1 | 9/2009 | Vlietinck | |
| 2009/0245610 A1 | 10/2009 | Can et al. | |
| 2010/0054556 A1 | 3/2010 | Novatzky | |
| 2010/0060652 A1 | 3/2010 | Karlsson | |
| 2010/0123733 A1 | 5/2010 | Zaharia | |
| 2010/0174823 A1 | 7/2010 | Huang | |
| 2010/0272342 A1 | 10/2010 | Berman et al. | |
| 2010/0278405 A1 | 11/2010 | Kakadiaris et al. | |
| 2011/0044524 A1 | 2/2011 | Wang et al. | |
| 2011/0112862 A1* | 5/2011 | Yu | G06Q 50/24 |
| | | | 705/3 |
| 2012/0078088 A1 | 3/2012 | Whitestone et al. | |
| 2012/0226916 A1* | 9/2012 | Hahn | G16H 10/60 |
| | | | 713/193 |
| 2012/0233153 A1* | 9/2012 | Roman | G06F 16/2393 |
| | | | 707/722 |
| 2013/0176319 A1 | 7/2013 | Westerhoff | |
| 2013/0195329 A1 | 8/2013 | Canda | |
| 2015/0213288 A1* | 7/2015 | Bilodeau | G06F 16/9535 |
| | | | 726/26 |
| 2015/0286791 A1* | 10/2015 | Altobello | G16H 40/67 |
| | | | 705/3 |
| 2016/0012181 A1 | 1/2016 | Massey | |
| 2017/0011514 A1 | 1/2017 | Westerhoff | |
| 2017/0346883 A1 | 3/2017 | Westerhoff | |
| 2017/0098329 A1 | 4/2017 | Westerhoff | |
| 2017/0104811 A1 | 4/2017 | Westerhoff | |
| 2017/0178593 A1 | 6/2017 | Westerhoff | |

FOREIGN PATENT DOCUMENTS

| | | |
|---|---|---|
| EP | 0502187 | 9/1992 |
| EP | 0611181 | 8/1994 |
| EP | 0476070 | 8/1996 |
| EP | 0925556 | 6/1999 |
| EP | 0953943 | 11/1999 |
| EP | 0964 366 | 12/1999 |
| EP | 187340 | 3/2001 |
| EP | 2098895 | 9/2009 |
| EP | 2098994 | 9/2009 |
| WO | WO9016072 | 12/1990 |
| WO | WO9102320 | 2/1991 |
| WO | WO9205507 | 4/1992 |
| WO | WO9642022 | 12/1996 |
| WO | WO9810378 | 3/1998 |
| WO | WO9812667 | 3/1998 |
| WO | WO9833057 | 7/1998 |
| WO | WO0120546 | 3/2001 |
| WO | WO0134027 | 5/2001 |
| WO | WO11065929 | 6/2001 |
| WO | WO0163561 | 8/2001 |
| WO | WO0174238 | 10/2001 |
| WO | WO0185022 | 11/2001 |
| WO | WO0241760 | 5/2002 |
| WO | WO02067201 | 8/2002 |
| WO | WO02082065 | 10/2002 |
| WO | WO03061454 | 7/2003 |
| WO | WO03088133 | 10/2003 |
| WO | WO03090171 | 10/2003 |
| WO | WO03098539 | 11/2003 |
| WO | WO04019782 | 3/2004 |
| WO | WO04020996 | 3/2004 |
| WO | WO04020997 | 3/2004 |
| WO | WO04034087 | 4/2004 |
| WO | WO04044848 | 5/2004 |
| WO | WO04066215 | 8/2004 |
| WO | WO04072906 | 8/2004 |
| WO | WO05071601 | 8/2005 |
| WO | WO09029636 | 3/2009 |
| WO | WO09067675 | 5/2009 |
| WO | WO09067680 | 5/2009 |

OTHER PUBLICATIONS

Wayland, Jennifer, Healthcare Data Masking: Tokenization, HIPAA, and More, [online], Published May 4, 2015, available at: < https://blogs.informatica.com/2015/05/04/healthcare-data-masking-primer/#fbid=WqRelKMticl > (Year: 2015).*

Aryanto et al., "Free DICOM de-identification tools in clinical resarch: functioning and safety of patient privacy" European Radiology, 25:3685-3695 (2015). (Year: 2015).*

PCT/EP2016/067886, Preliminary and International Search Reports, dated Jan. 17, 2017.

PCT/EP2016/067886, Preliminary and International Search Reports, dated Jan. 17, 2017, 18 pages.

Tao, W., Tomographic mammography using a limited number of low dose cone beam projection images, Medical Physics, AIP, Melville, NY vol. 30, pp. 365-380, Mar. 2003, ISSN: 0094-2405.

Wikipedia, Anonymous, 'Volume Rendering' May 30 2015, retrieved Nov. 4 2016, https://en.wikipedia.org/w/index.php?title=Volume_rendering&oldid=664765767.

Wikipedia, Anonymous, 'Tomographic Reconstruction' Dec. 6 2014, retrieved Nov. 4 2016, https://en.wikipedia.org/w/index.php?title=Tomographic_Reconstruction&oldid=636925688.

https://www.biotechniques.com/bioinformatics-computational-biology/big-data-in-big-trouble/ "Big Data in big trouble?", BioTechniques, Sep. 13, 2019.

Re-identification of court decisions by linkage of data banks, Jusletter 2 (2019) by Kerstin Noëlle Volkinger et al.

Jusletter 2 (2019) machine translation of abstract.

ATI Website Index, http://www.ati.com/developer/index.html, Dec. 20, 2002, 2 pages.

Cabral et al., Accelerated Volume Rendering and Tomographic Reconstruction Using Texture Mapping Hardware*, Silicon Graphics Computer Systems, 1995 IEEE, DD. 91-97.

Carr, Nathan A., Jesse D. Hall, John C. Hart, The ray engine, Proceedings of the ACM SIGGRAPH/EUROGRAPHICS conference on Graphics hardware, Sep. 1-2, 2002, pp. 37-46.

Chidlow, et al, Rapid Emission Tomography Reconstruction, Proceedings of the 2003 Eurographics/IEEE TVCG Workshop on Volume Graphics, Tokyo, Japan, Jul. 7-8, 2003, 13 pages.

Cohen, Michael, et al., A Progressive Refinement Approach to Fast Radiosity Image Generation, Computer Graphics, vol. 22, No. 4, Aug. 1988, pp. 75-84.

Corner, B., University of Nebraska-Lincoln, MatLab.txt, 2003, 1 page.

Dachille, et al., High-Quality Volume Rendering Using Texture Mapping Hardware, Siggraph/Eurographics Hardware Workshop (1998) (8 pages).

Dempster, et al., Maximum Likelihood From Incomplete Data Via the EM Algorithm, Harvard University and Educational Testing Service, Dec. 8, 1976, pp. 1-38.

Dennis, C, et al. Overview of X-Ray Computed Tomography, http://www.howstuffworks.com/framed.htm?parent=c...tm&url=http://www.ctlab.geo.utexas.edu/overview/, Dec. 26, 2002, 5 pages.

Dobbins, et al., Digital X-Ray Tomosynthesis: Current State of the Art and Clinical Potential, Physics in Medicine and Biology, vol. 48, pp. R65-R106 (2003).

Doggett, Michael, ATI, Programmability Features of Graphics Hardware, (paper) Apr. 23, 2002, pp. C1-C22.

Doggett, Michael, ATI, Programmability Features of Graphics Hardware, (slideshow) slides 1-62 31 pages.

(56) References Cited

OTHER PUBLICATIONS

Du, H., Sanchez-Elez, M., Tabrizi, N., Bagherzadeh, N., Anido, M. L., and Fernandez, M. 2003. Interactive ray tracing on reconfigurable SIMD MorphoSys. In Proceedings of the 2003 Conference on Asia South Pacific Design Automation (Kitakyushu, Japan, Jan. 21-24, 2003). ASPDAC. ACM, New York, NY, 471-476.
Eldridge Matthew, Homan Igehy, Pat Hanrahan, Pomegranate: a fully scalable graphics architecture, Proceedings of the 27th annual conference on Computer graphics and interactive techniques, p. 443-454, Jul. 2000.
Fang, L., et al., Fast Maximum Intensity Projection Algorithm Using Shear Warp Factorization and Reduced Resampling, Mangetic Resonance in Medicine 47:696-700 (2002).
Filtered Backprojection Reconstruction, http://www.physics.ubd.ca/-mirg/home/tutorial/fbDrecon.html, 216/2003, 5 pages.
Goddard et al., High-speed cone-beam reconstruction: an embedded systems approach, 2002, SPIE vol. 4681, pp. 483-491.
Grass et al., Three-dimensional reconstruction of high contrast objects using C-arm image intensifier projection data, 1999, Computerized Medical Imaging and Graphics, 23, pp. 311-321.
Hadwiger, Markus, et al., Hardware-Accelerated High-Quality Reconstruction of Volumetric Data on PC Graphics Hardware, VRVis Research Center, Vienna, Austria, and Institute of Computer Graphics and Algorithms, Vienna University of Technology, Austria, 9 pages.
Hastreiter et al. (Integrated registration and visualization of medical image data, Proc. Computer Graphics International, Jun. 22-26, 1998, pp. 78-85).
Hopf, M., Ertl, T., Accelerating 3d Convolution Using Graphics Hardware, Proc. IEEE Visualization, 1999, 5 pages.
Hudson, et al., Accelerated Image Reconstruction Using Ordered Subsets of Projection Data, IEEE Transactions on Medical Imaging, vol. 13, No. 4, Dec. 1994, pp. 601-609.
Image Registration Slideshow, 105 pages.
Iterative definition, Merriam-Webster on-line dictionary, printed Aug. 26, 2010, 3 pages.
Jain, Anju, A Programmable Graphics Chip, pcquest.com, Jun. 18, 2001.
Jones et al., Positron Emission Tomographic Images and Expectation Maximization: A VLSI Architecture for Multiple Iterations Per Second, Computer Technology and Imaging, Inc., 1988 IEEE, pp. 620-624.
Kajiya, J. T., Ray tracing volume densities, Proc. Siggraph, Jul. 1984, Computer Graphics, vol. 18, No. 3, pp. 165-174.
Karlsson, Filip; Ljungstedt, Carl Johan; Ray tracing fully implemented on programmable graphics hardware, Master's Thesis, Chalmers University of Technology, Dept. of Computer Engineering, Goteborg, Sweden, copyright © 2004, 29 pages.
Kruger J. and R. Westermann, Acceleration Techniques for GPU-based Volume Rendering, Proceedings of IEEE Visualization, 2003, 6 pages.
Lange et al., EM Reconstruction Algorithms for Emission and Transmission Tomography, J Computer Assisted Tomography 8, DD. 306, et seq. (1984).
Lange et al., Globally Convergent Algorithms for Maximum a Posteriori Transmission Tomography, IEEE Transactions on Image Processing, Vo. 4, No. 10, Oct. 1995, pp. 1430-1438.
Li et al., Tomographic Optical Breast Imaging Guided by Three-Dimensional Mammography, Applied Optics, Sep. 1, 2003, vol. 42, No. 25, pp. 5181-5190.
Li, et al., a Brick Caching Scheme for 30 Medical Imaging, Apr. 15-18, 2004, IEEE International Symposium on Biomedical Imaging: Macro to Nano 2004, vol. 1, pp. 563-566.
Maes, et al. Multimodality Image Registration by Maximization of Mutual Information, IEEE Tran. on Medical Imaging, vol. 16, No. 2, Apr. 1997. pp. 187-198).
Max, N., Optical Models for Direct Volume Rendering, IEEE Transactions on Visualization and Computer Graphics, Jun. 1995, 1(2): pp. 99-108.
McCool, M. et al., Shader Algebra, 2004, pp. 787-795.

McCool, Michael J., Smash: A Next-Generation API for Programmable Graphics Accelerators, Technical Report CS-200-14, Computer Graphics Lab Dept. of Computer Science, University of Waterloo, Aug. 1, 2000.
Microsoft, Architectural Overview Direct for 3D, http://msdn.microsoft.com/library/default.asp?url=/library/en-us/dx8_c/directx_cpp/Graphics/ProgrammersGuide/GettingStarted/Architecture, 12120/2002, 22 pages.
Mitchell, Jason L., RadeonTM 9700 Shading, SIGGRAPH 2002—State of the Art in Hardware Shading Course Notes, DD.3.1-1-3.1-39, 39 pages.
Mitschke et al., Recovering the X-ray projection geometry for three-dimensional tomographic reconstruction with additional sensors: Attached camera versus external navigation system, 2003, Medical Image Analysis, vol. 7, pp. 65-78.
Mueller, K., and R. Yagel, Rapid 3-D Cone Beam Reconstruction With the Simultaneous Algebraic Reconstruction Technique (Sart) Using 2-D Texture Mapping Hardware, IEEE Transactions on Medical Imaging, Dec. 2000, 19(12): pp. 1227-1237.
Navab, N., et al., 3D Reconstruction from Projection Matrices in a C-Arm Based 3D-Angiography System, W.M. Wells e al., eds., MICCAI'98, LNCS 1496, pp. 119-129, 1998.
Parker, S., et al., Interactive Ray Tracing for Isosurface rendering, IEEE, 1998, pp. 233-258.
PCT/US2008/084282, Preliminary and International Search Reports, dated May 11, 2011.
PCT/US2005/000837, Preliminary and International Search Reports, dated May 11, 2005.
PCT/US2008/74397, Preliminary and International Search Reports, dated Dec. 3, 2008.
PCT/US2008/84368, Preliminary and International Search Reports, dated Jan. 13, 2009.
PCT/US2008/84376, Preliminary and International Search Reports, dated Jan. 12, 2009.
Pfister, H., et. al., The VolumePro real-time ray-casting System, Computer Graphics Proceedings of SIGGRAPH), Aug. 1999, No. 251-260.
Phong, B. T. Illumination for Computer Generated Pictures, Communications of the ACM, 18(6), Jun. 1975, pp. 311-317.
Porter, D. H. 2002. Volume Visualization of High Resolution Data using PC-Clusters. Tech. rep., University of Minnesota. Available at http://www.lcse.umn.edu/hvr/pc_vol_rend_L.pdf.
Potmesil, M. and Hoffert, E. M. 1989. The pixel machine: a parallel image computer. In Proceedings of the 16th Annual Conference on Computer Graphics and interactive Techniques SIGGRAPH '89. ACM, New York, NY, 69-78.
Purcell, T., et al., Real-time Ray Tracing on Programmable Graphics Hardware, Department of Computer Science, Stanford University, Stanford, CA, Submitted for review to SIGGRAPH 2002, 2002. http://graphics.stanford.edu/papers/rtongfx/rtongfx_submit.pdf.
Purcell, T., et. al., Ray tracings on Programmable Graphics Hardware, Computer Graphics (ProceedinQs of SIGGRAPH), 1998, pp. 703-712.
Purcell, Timothy J., Craig Donner, Mike Cammarano , Henrik Wann Jensen , Pat Hanrahan, Photon mapping on programmable graphics hardware, Proceedings of the ACM SIGGRAPH/EUROGRAPH-ICS conference on Graphics hardware, Jul. 26-27, 2003, 11 pages.
Ramirez et al. (Prototypes stability analysis in the design of a binning strategy for mutual information based medical image registration, IEEE Annual Meeting of the Fuzzy Information, Jun. 27-30, 2004, vol. 2, pp. 862-866.
Rib Cage Projection, downloaded from http://www.colorado.edu/physics/2000/tomography/final_rib_cage.html on Dec. 26, 2002, 3 pages.
Roettger, Stefan, et al., Smart Hardware-Accelerated Volume Rendering, Joint Eurographics—IEEE TCVG Symposium on Visualization, 2003, pp. 231-238, 301.
Sandborg, Michael, Computed Tomography: Physical principles and biohazards, Department of Radiation Physics, Faculty of Health Sciences, Linkoping University, Sweden, Report 81 ISSN 1102-1799, Sep. 1995 ISRN ULI-RAD-R--81--SE, 18 pages.

(56) References Cited

OTHER PUBLICATIONS

Sarrut et al. (Fast 30 Image Transformations for Registration Procedures, Proc. lnt'I Conf. on Image Analysis and Processing, Sep. 27-29, 1999, pp. 446-451.
Selldin, Hakan, Design and Implementation of an Application Programming Interface for Volume Rendering, Linkooings Universitet.
Shekhar, R.; Zagrodsky, V., Cine MPR: interactive multiplanar reformatting of four-dimensional cardiac data using hardware-accelerated texture mapping, IEEE Transactions on Information Technology in Biomedicine, vol. 7, No. 4, pp. 384-393, Dec. 2003.
Silver, et al., Determination and correction of the wobble of a C-arm gantry, Medical Imaging 2000: Image Processing, Kenneth M. Hanson, ed., Proceedings of SPIE vol. 3970 (2000).
Stevens, Grant, et al., Alignment of a Volumetric Tomography System, Med. Phys., 28 (7), Jul. 2001.
Tasdizen, T. , Ross Whitaker, Paul Burchard , Stanley Osher, Geometric surface processing via normal maps, ACM Transactions on Graphics (TOG), v.22 n. 4, p. 1012-1033, Oct. 2003.
Tasdizen, T.; Whitaker, R.; Burchard, P.; Osher, S.; Geometric surface smoothing via anisotropic diffusion of normals, IEEE Visualization, VIS 2002, Nov. 2002, pp. 125-132.
Technical Brief: NVIDIA nfiniteFX Engine: Programmable Pixel Shaders, NVIDIA Corporation, 5 pages.
Technical Brief: NVIDIA nfiniteFX Engine: Programmable Vertex Shaders, NVIDIA Corporation, 12 pages.
Viola, I, et al., Hardware Based Nonlinear Filtering and Segmentation Using High Level Shading Languages, Technical Report TR-186-2-03-07, May 2003, 8 pages.
Viola, P., Alignment by Maximization of Mutual Information, PhD Thesis MIT (Also Referred to As—AI Technical report No. 1548), MIT Artificial Intelligence Lab, Jun. 1, 1995, pp. 1-29.
Weiler, M, M. Kraus and T. Ertl, Hardware-Based View-Independent Cell Projection, Proceedings IEEE Symposium on Volume Visualization 2002, pp. 13-22.
Weiler, M. et al., Hardware-based ray casting for tetrahedral meshes, IEEE Visualization, VIS 2003, Oct. 24-24, 2003, pp. 333-340.
Weiler, M. et al., Hardware-Based view-Independent Cell Projection, IEEE, 2002, pp. 13-22.
Weiskopf, D., T. Schafhitzel, T. Ertl, GPU-Based Nonlinear Ray Tracing, EUROGRAPHICS, vol. 23, No. 3, Aug. 2004.
Wen, Junhai; Zigang Wang; Bin Li; Zhengrong Liang; An investigation on the property and fast implementation of a ray-driven method for inversion of the attenuated Radon transform with variable focusing fan-beam collimators, 2003 IEEE Nuclear Science Symposium Conference Record, vol. 3, Oct. 19-25, 2003, pp. 2138-2142.
Wu et al., Tomographic Mammography Using a Limited Number of Low-dose Conebeam Projection Images, Med. Phys., pp. 365-380 (2003).
Xu et al., Toward a Unified Framework for Rapid 30 Computed Tomography on Commodity GPUs, Oct. 19-25, 2003, IEEE Nuclear Science Symposium Conference 2003, vol. 4, pp. 2757-2759.
Xu et al., Ultra-fast 30 Filtered Backprojection on Commodity Graphics Hardware, Apr. 1-18, 2004, IEEE International symposium on Biomedical Imaging: Macro to Nano, vol. 1, pp. 571-574 and corresponding power point presentation.

\* cited by examiner

○ ○ ○     Media Exporter

Patient
Name: De-identified
Actual data size: ~14 MB

Options
Destination: [Export files to local client folder ▾]
Export Folder: [/Users/johnson/Media Export] [Browse]
Media Folder: [2015-07-26-001]
☐ Include Media Viewer   ☐ Autorun Media Viewer   ☐ Uncompressed only (IHE)
☑ De-Identify [Details...]

Progress
File transfer not started.
[                    ] 0%

[Make Default]     [Export] [Close]

FIG. 3A

| DICOM Tag | Description | New Value | < | Old Value |
|---|---|---|---|---|
| Patient 1 | | | | |
| 0010-0010 | Patient Name | De-identified | < | SMITH^MARY^F^^ |
| 0010-0020 | Patient ID | f59c4a5c | < | PAT12345 |
| 0010-0030 | Patient Birth Date | 19320101 | < | 19320509 |
| Study 1 | | | | |
| 0008-0050 | Accession Number | 1c457efc | < | EXM5678 |
| 0020-0010 | Study ID | a43ee1b2 | < | EXM5678 |
| 0008-1030 | Study Description | THORAX AP | < | THORAX AP |
| 0032-4000 | Study Comments | | < | |
| 0008-0080 | Institution Name | | < | SPRINGFILD ENERAL HOSPITAL |

De-identification Details

☑ Remove other demographic tags     ☑ Remove private tags

[ OK ]   [ Cancel ]

FIG. 3B

METHOD AND APPARATUS FOR ANONYMIZED DISPLAY AND DATA EXPORT

PRIORITY CLAIM

This application claims priority to U.S. Provisional application No. 62/199,630 filed Jul. 31, 2015, the specification and drawings of which are herein expressly incorporated by reference in its entirety.

FIELD OF INVENTION

The invention pertains to novel ways of anonymizing reports including medical diagnosis reports containing protected health information.

BACKGROUND

In modern medicine, medical diagnosis reports are often digitized and contain information relating to the patient. Medical diagnosis reports include reports from clinical software systems such as in the field of radiology, where images are increasingly acquired and processed digitally. Picture Archiving and Communications Systems (PACS), Radiology Information Systems (RIS) and similar computer systems are used to process and store the image data, as well as the patient information related to the images. The related information includes patient demographics, location and time of acquisition and other acquisition parameters. This non-pixel information is referred to as meta-data.

The meta-data is important for data management, e.g. for searching or identifying a particular data set relating to a particular exam, and it provides important information about the examination, which is relevant for the diagnostic interpretation of the images. Part of the meta-data (the Patient Identifiable Information (PII) and the Protected Health Information (PHI)) relate to the particular patient and allows identification of the patient.

SUMMARY OF THE INVENTION

In an embodiment of the present invention, a method for anonymizing protected health information present in medical diagnostic reports is outlined. In an embodiment of the present invention, users with the appropriate permission based on their user ID can launch a function inside a system in order to anonymize and export the currently loaded study or studies, or one or more studies identified by a search criteria. The data from the studies that were identified is then anonymized on the system. In an embodiment of the present invention, the data from selected studies is anonymized on a server, and only then transmitted to another network device or stored to a hard disk or other media.

BRIEF DESCRIPTION OF THE DRAWINGS

This invention is described with respect to specific embodiments thereof. Additional features can be appreciated from the Figures in which:

FIG. 3A shows an artist's impression of a dialog for exporting an exam with a De-Identification option, according to an embodiment of the invention;

FIG. 3B shows an artist's impression of the dialog to configure the De-Identification details, according to an embodiment of the invention.

DESCRIPTION OF THE INVENTION

Definitions

Figure 1:
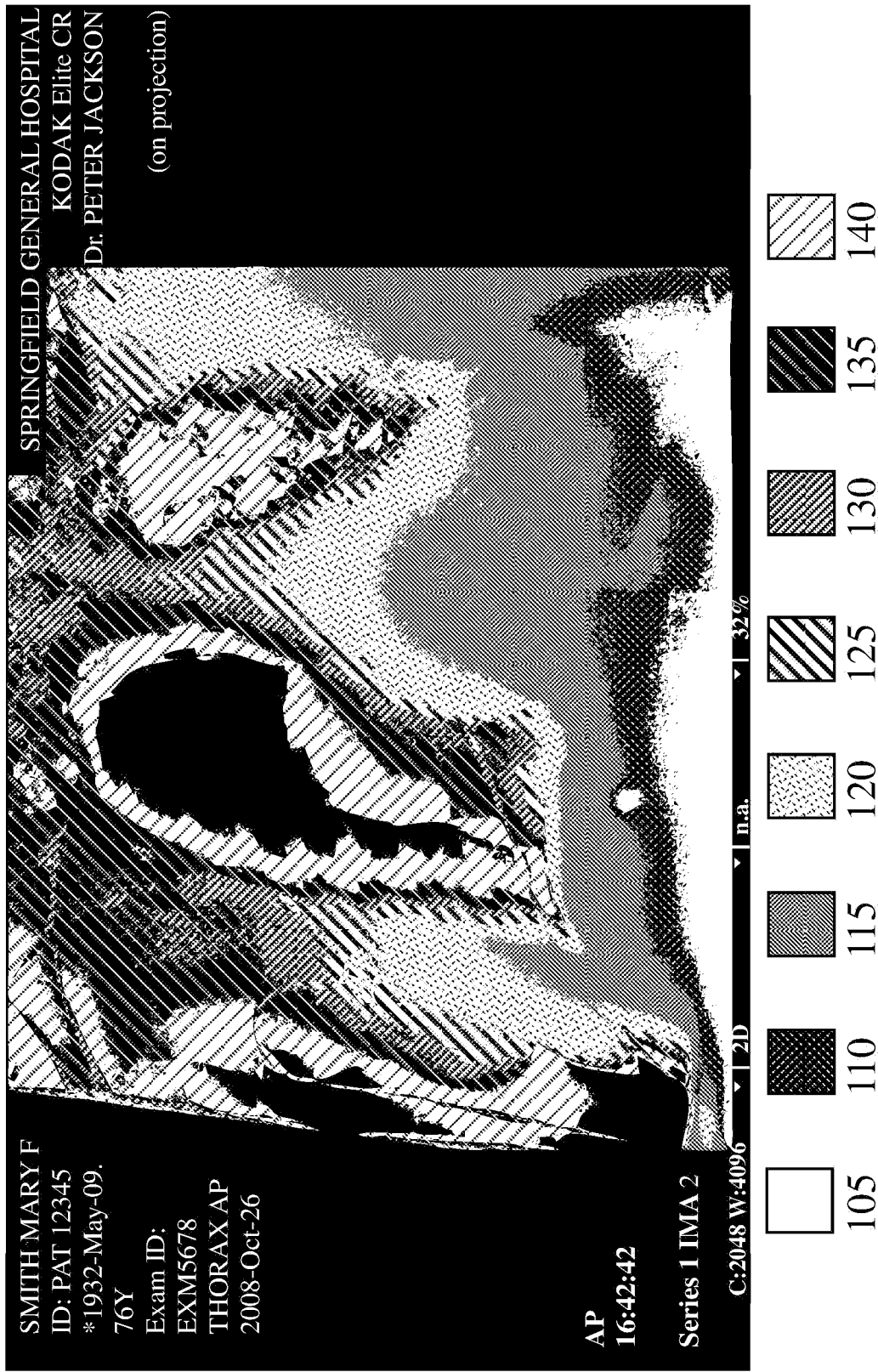
FIG. 1 shows an artist's impression of a medical report with pseudo-Patient Identifiable Information (pseudo-PII), according to an embodiment of the invention.

The transitional term 'comprising' is synonymous with 'including', 'containing', or 'characterized by' is inclusive or open-ended and does not exclude additional, unrecited elements or method steps.

The transitional phrase 'consisting of' excludes any element, step, or ingredient not specified in the claim, but does not exclude additional components or steps that are unrelated to the invention such as impurities ordinarily associated with a composition.

The transitional phrase 'consisting essentially of' limits the scope of a claim to the specified materials or steps and those that do not materially affect the basic and novel characteristic(s) of the claimed invention.

The term 'client-server' refers to a computer system that selectively shares its resources; a client is a computer or computer program that initiates contact with a server in order to make use of a resource. This sharing of computer resources allows multiple people to use a computer server at the same time. Because a computer does a limited amount of work at any moment, a time-sharing system must quickly prioritize its tasks to accommodate the clients. Clients and servers exchange messages in a request-response messaging pattern: The client sends a request, and the server returns a response.

The phrase 'metadata entry' means data associated with a specific parameter in a medical diagnosis report. Metadata comprises both structural metadata and descriptive metadata. Structural metadata is information about the data. Descriptive metadata is the information content of the data.

The phrase 'phi of metadata' refers to PHI or PII in a medical diagnostic report. The phi of metadata is the information which makes up the descriptive metadata of a metadata entry related to PHI or PII.

The phrase 'institution aware ID' is a code that can be used to identify an institution for which the particular user ID is a member. An institution aware ID can be added to a phi of metadata to distinguish anonymized data from two separate institutions.

The phrase 'medical diagnosis' is the process of determining which disease or condition explains a person's symptoms and signs. The information required for diagnosis is typically collected from a medical history and physical examination of the person seeking medical care.

The phrase 'medical diagnostic report' means a report associated with a medical diagnosis where the medical diagnostic report contains data including protected health information pertaining to the name, age and/or sex of the patient, medical history, physical examination and/or medical diagnosis of the patient, where at least some of the data is computer readable.

The term 'retrieving' means a process whereby a processor reads one or more phi of metadata from a medical diagnostic report.

The term 'accessing' means a process whereby a processor reads one or more phi of metadata from a medical diagnostic report and stores the one or more phi of metadata in one or more volatile computer memory locations.

The phrase 'server side cache' means cache associated with the server processor which is not directly accessible by a client processor.

The phrase 'Protected Health Information', 'PHI', 'Patient Identifiable Information' or 'PII' are defined as the terms are used in the Health Insurance Portability and Accountability Act of 1996 (HIPAA) and other regulations relating to maintaining the privacy and security of individually identifiable health, financial or other information including Gramm-Leach-Bliley Act (GLBA), Federal Education Rights and Privacy Act (FERPA), Children's Online Privacy Protection Act (COPPA), Fair Credit Reporting Act (FCRA) the Health Information Technology for Economic and Clinical Health (HITECH) Act enacted as part of the American Recovery and Reinvestment Act of 2009 (ARRA), the Genetic Information Nondiscrimination (GINA) Act and other modifications of the HIPAA Rules. 'PHI' or 'PII' is any information that can be used on its own or with other information to identify, contact, locate or identify: a patient, a health status, a provision of health care or a payment for health care irrespective of how it is obtained and whether it is collected by or on behalf of an institution.

The term 'display' means in the context of aspects and embodiments disclosed herein and refers in the usual and customary sense to physical representation of data e.g. a printed page or an electronic representation on a visual display monitor, a cathode ray oscilloscope, a liquid crystal display, a nixie tube, a light emitting diode display, a plasma display and the like.

The phrase 'combined value' means merging two or more phi of metadata, where each field of the one or more phi of metadata and their settings are copied into a new metadata field.

The term 'concatenating' means adding a separator character that is not part of the one or more phi of metadata to the one or more phi of metadata.

The phrase 'changing one or more phi of metadata' means adding computer readable data to one or more phi of metadata or deleting computer readable data from one or more phi of metadata, e.g., concatenating or combining.

The phrase 'separator character' means a designated computer readable character used to change one or more phi of metadata of the computer readable data by adding the separator character to the one or more phi of metadata, where the separator character is otherwise not used in the one or more phi of metadata.

The term 'computing' means using a Central Processing Unit (CPU) or Graphics Processing Unit (GPU) to perform a calculation.

The phrase 'volatile computer memory location' means a memory location in a data structure which requires power to maintain the stored information such as volatile random access memory. The volatile computer memory location retains its contents only while the computer is connected to power. When the power is interrupted the stored data is immediately lost. When the volatile computer memory location is changed by adding or removing information, the memory location is overwritten. The word 'overwritten' means replacement of data in a data structure thereby removing the previous data and replacing it with the provided data.

The phrase 'secure value' means one or more phi of metadata corresponding to one or more protected health information values for which the one or more phi of metadata have been changed such that the protected health information cannot be ascertained.

The term 'anonymization' means to remove the possibility of ascertaining protected health information values from a medical diagnostic report.

The phrase 'deidentified patient data' means a medical diagnostic report in which all PII and/or PHI values have been changed such that the PHI and/or PHI cannot be ascertained.

The term 'Study' will be used to refer to the set of images produced by an examination. In an embodiment of the invention, a Study consists of one or more images. In an alternative embodiment of the invention, a Study consists of two or more images. The images can be grouped into one or more image series. Each image, each series, and the whole Study can have different parameters attached. For medical images these can be defined by the Digital Imaging and Communication in Medicine (DICOM) standard.

The phrase 'Hanging Protocol' will be used to refer to specific conventions how X-Ray films are arranged (hung) at a light box.

The phrase 'Display Protocol' will be used to refer to the way images are displayed in a computer system, specifically the selection of the images to be displayed, the layout of the images, as well as the rendering parameters and styles.

The term 'view' or 'viewing' means a display of a 3D or 2D image. The phrases 'viewing position' or 'viewing ray' refer to a display of a 3D or 2D image as observed from the viewing position, i.e., along a line defined by the viewing ray.

The term 'Viewport' will be used to refer to the logical part of the screen on the client computer in which a particular View is displayed, for example the user interface on the client computer can contain four rectangular Viewports 1160 of which three show a frontal, left, and bottom view respectively of a particular data, while the fourth viewer might show a 2D cross section through the same or a different data set.

The phrase 'Sets of Images' or 'Image Set' will be used to refer to one or more images, selected based on the rules.

The phrase 'Study Selection Rules' will be used to refer to the rules used to select and access the studies to be displayed including the anonymization of PHI and PII.

The phrase 'Protocol Selection Rules' will be used to refer to the rules used to select the layout of the images to be displayed.

The phrase 'Image Set Rules' will be used to refer to the rules used to form Image Sets 1165 from the images of one or more Study by applying selection, sorting, and breaking rules.

The phrase 'Style Rules' will be used to refer to the rules to determine which rendering type, rendering style, and rendering parameters are used for a particular Image Set 1165 in a particular viewer.

The phrase 'patient ID' refers to a code used to identify an individual patient.

The phrase 'user ID' refers to the access permissions associated with an individual user.

The phrase 'displaying a listing' or 'listing' means displaying a code or other abbreviated representation of a medical diagnostic report such that it can be selected, where displaying the listing does not display or otherwise access the information contained in the medical diagnostic report. Displaying the listing can be used to select the medical diagnostic report for viewing or other access.

The phrase 'displaying a medical diagnostic report' means displaying a medical diagnostic report such that the medical information but not necessarily the PII is displayed.

The phrase 'pseudo-Patient Identifiable Information' or 'pseudo-PII' means information that is used to simulate PII or PHI. Pseudo-PII does not and cannot function as PII or PHI. Pseudo-PII appears in the same format as PII or PHI, but because it is simulated it cannot be used on its own or with other information to identify, contact, locate or identify: a patient, a health status, a provision of health care or a payment for health care. Pseudo-PII rather than PII or PHI is displayed in this application in accordance with HIPAA, The Privacy Act, ARRA, COPPA, FERPA, FCRA, GLBA and HITECH to exemplify PII or PHI and the invention is applied to this pseudo-PII rather than to PII or PHI. Because the pseudo PII is in a similar format to the PII or PHI, the pseudo-PII can be used to exemplify the anonymization of PII or PHI using the invention.

The phrase 'Volume Rendering' will be used to refer to Volume Rendering techniques including shaded Volume Rendering techniques, maximum intensity projection (MIP), oblique slicing or multi-planar reformats (MPR), axial/sagittal and coronal slice display, and thick slices (also called slabs). In medical imaging, for example, Volume Rendering is used to display 3D images from 3D image data sets, where a typical 3D image data set is a large number of 2D slice images acquired by a CT or MRI scanner and stored in a data structure.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes. Furthermore, it will also be apparent that the present invention is not limited to any particular software programming language or programming paradigm.

While critical for the clinical workflow, there are a number of scenarios where no PII is required and the presence of the PII is even problematic. Due to health data and general privacy legislation, handling PII and passing on PII to other parties is often not possible, or comes with significant legal and contractual burden and potentially a business risk. The business risk is accentuated when the medical diagnosis report with the PII are shipped 'off shore' as the interpretation of what constitutes reasonable business practices can become subject to additional legal jurisdictions.

Examples for such scenarios include: scientific work, presentations in education, technical support and troubleshooting of problems in PACS, Imaging Workflow Solution, RIS, or similar computer systems, or generation of test data for software testing.

One approach to address the requirement for medical diagnosis reports without PII is to send images to a system for data anonymization, which creates a copy of the images, and strips the meta-data contained in the images or replaces them with default values. Such default value could be a patient ID of '00000', or an incrementing value such as ANON001, ANON002, . . . .

This approach has a number of problems, which the present invention addresses. Firstly, the workflow of sending images to another system to anonymize, then export the data is cumbersome.

Secondly, anonymizing images individually, and individually deleting the patient identifiers or replacing them with default or random values, results in loss of any correlation information between multiple studies belonging to the same patient. In many cases, e.g. scientific use of the data, this is undesirable. This can be tackled by storing a table that maps real patient-identifiers to anonymized ones. This process is often referred to as 'pseudonymization'. Pseudonymization allows for re-identification of the anonymized data. However, for the same reasons that PII sharing can be undesirable, the ability to re-identify anonymized data through pseudonymization can be undesired. The present invention offers an alternative way to share medical diagnosis reports without the ability to re-identify PII.

Instead of mapping the patient ID to simple default values, the present invention uses a novel approach. A secure hash algorithm (SHA), such as SHA-1 is applied to the concatenation of a selected set of metadata fields. Typical sets of metadata fields are:

Patient ID;

Patient Name, Patient Birth Date, and patient gender; or

Patient ID, Patient Name, Patient Birth Date, and patient gender.

The phrase 'secure hash function' means a hash function in which it is impossible to invert, that is, to recreate the input data from its hash value alone. Examples of secure hash function include MD4, MD5, SHA-1, SHA-2, Skein, and BLAKE.

The secure hash function has three main properties. Firstly, it is easy to compute the hash value for any given message. Secondly, it is not feasible to generate a message from its hash. Thirdly, it is not feasible to modify a message without changing the hash.

One secure hash function, Hashcash, uses partial hash inversions to prove that work was done, as a message which can be sent. Many secure hash functions, including MD4, MD5, SHA-1, SHA-2 and SHA-3 finalists Skein and BLAKE are built from block-cipher. Alternatively, the secure hash function Keccak, was built on a cryptographic sponge. Further, a standard block cipher such as AES can be used to build a secure hash function.

In an embodiment of the present invention, in order to compute the secure hash function on a given set of fields, the field values are concatenated, using a separator character that is not used in the phi or that is not part of the field values, such as for example a backslash '/'. In an embodiment of the present invention, let C be the concatenated value of the selected fields. Then M=SHA1(C) is the mapped ID, that is used in the anonymized data set, where SHA1 is the SHA-1 secure hash function, or another type of secure hash function. In an alternative embodiment of the present invention, an alternative secure hash function selected from the group consisting of MD4, MD5, SHA-2, Skein, BLAKE and AES is used.

FIG. 1 shows an artist's impression of a X-Ray image of a human thorax displayed in a PACS viewer. In FIG. 1, the darkness of the X-Ray image is indicated using a grey scale shading system where 105 is white, black is black and the values 110, 115, 120, 125, 130, 135 and 140 indicate shades of gray from lightest to darkest. The relevant information, including patient demographics is shown as text overlays. FIG. 1 depicts the display of a non-anonymized data set. Note in FIG. 1 the PII (including the names and dates) shown are pseudo-PII for the sake of illustrating the invention, and are not a real patient's PII. The Imaging Device Name corresponds with the device used to measure the displayed X-Ray image, however the invention can be used for other manufacturer's X-Ray image devices, for other PACS devices, for other diagnostic reports, for other medical reports and for other non-medical reports.

FIG. 1 shows an artist's impression of a medical report with PII on the top left, top right and lower left. On the top left of FIG. 1 the 'Patient Name' is shown as SMITH MARY F, the 'Patient ID' as 12345 1932-May-09.76Y, the 'Exam ID' as EXM5678, the 'Study (Exam) Description' as THORAX AP, and the 'Study Date' as 2008-Oct-26. FIG. 1 also shows on the top right the 'Hospital Name' as SPRINGFIELD GENERAL HOSPITAL, the 'Imaging Device Name' KODAK Elite CR, and the 'Physician's Name' as Dr PETER JACKSON. Further, FIG. 1 shows on the lower left the 'Imaging Orientation' as AP, the 'Acquisition Time' as 16:42:42, and the 'Series/Image number' as 1 IMA 2.

Figure 2:
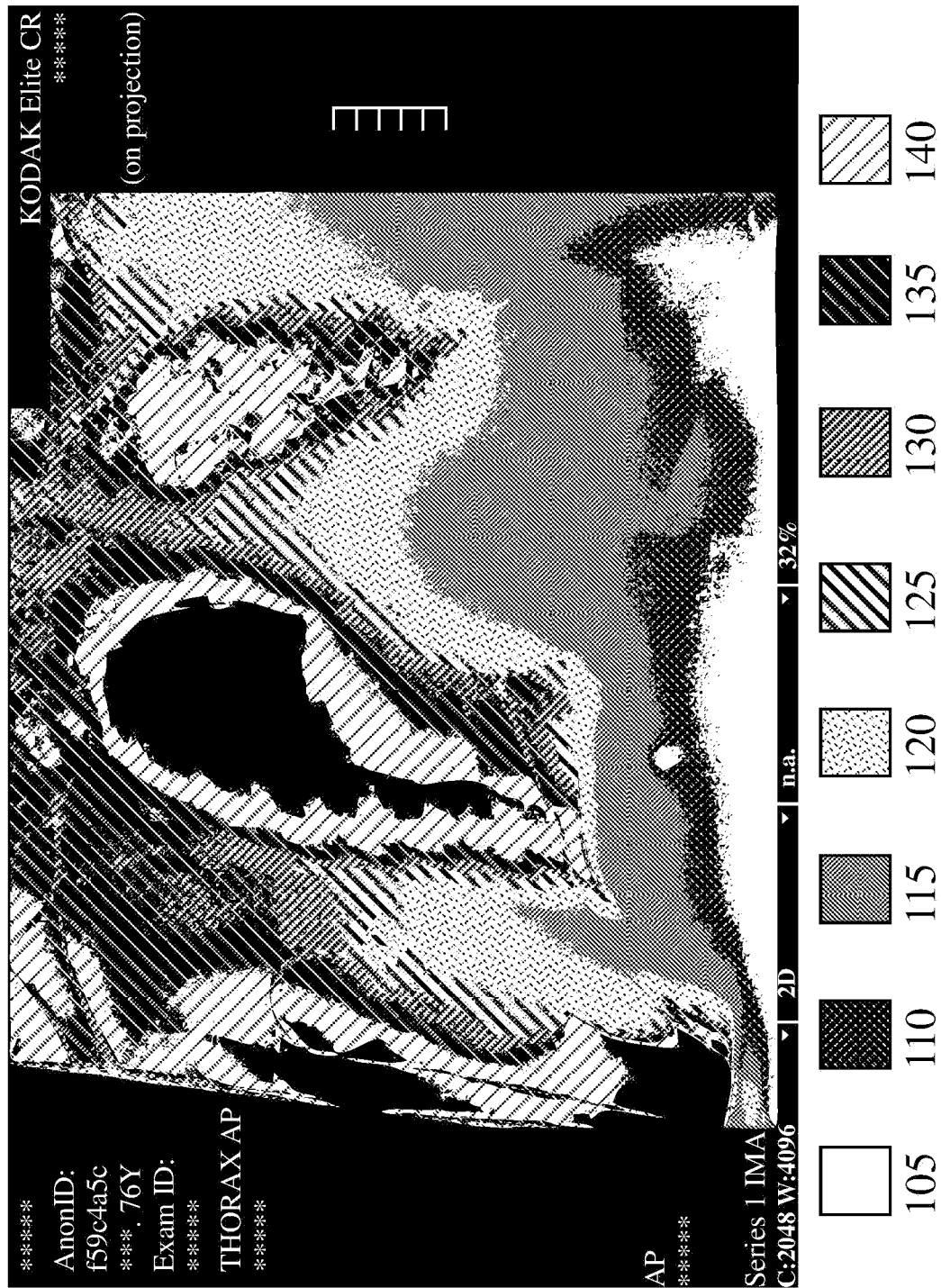
FIG. 2 shows an artist's impression of the medical report shown in FIG. 1 after anonymization in teaching mode, according to an embodiment of the invention.

FIG. 2 shows an artist's impression of the same study displayed when in the 'teaching mode'. In FIG. 2, the darkness of the image is indicated using a grey scale shading system where 105 is white, black is black and the values 110, 115, 120, 125, 130, 135 and 140 indicate shades of gray from lightest to darkest. In various embodiments of the invention, specific information is not displayed and replaced by "***" in the anonymized medical report when viewed in the teaching mode. On the top left in FIG. 2 the 'Patient Name' is *, the 'Patient ID' is replaced with 'AnonID' which is f59c4a5c*.76Y, the 'Exam ID' is *, the 'Study (Exam) Description' remains THORAX AP, and the 'Study Date' is *. On the top right, FIG. 2 does not show the 'Hospital Name', but still shows the 'Imaging Device Name' as KODAK Elite CR, and the 'Physician's Name' is *. Further, FIG. 2 shows on the lower left the 'Imaging Orientation' as AP, the 'Acquisition Time' is ***, and the 'Series/Image number' as 1 IMA 2. The Patient Birth Day is removed, but the patient's age (in years) is shown as 76Y.

In various embodiments of the invention the fields are configurable by a user. In alternative embodiments of the invention, the fields are configurable by a user based on their userID. The Patient ID (PAT12345) is not shown, and instead the mapped id (computed as described herein) is shown with a prefix of AnonID. Thus, as shown in FIG. 2, the PII associated with the medical diagnostic report shown in FIG. 1 can be removed according to an embodiment of the present invention.

Figure 4:
FIG. 4 shows an artist's impression of the medical report shown in FIG. 1 after export using the anonymization settings shown in FIG. 3B, according to an embodiment of the invention.
Figure 5:
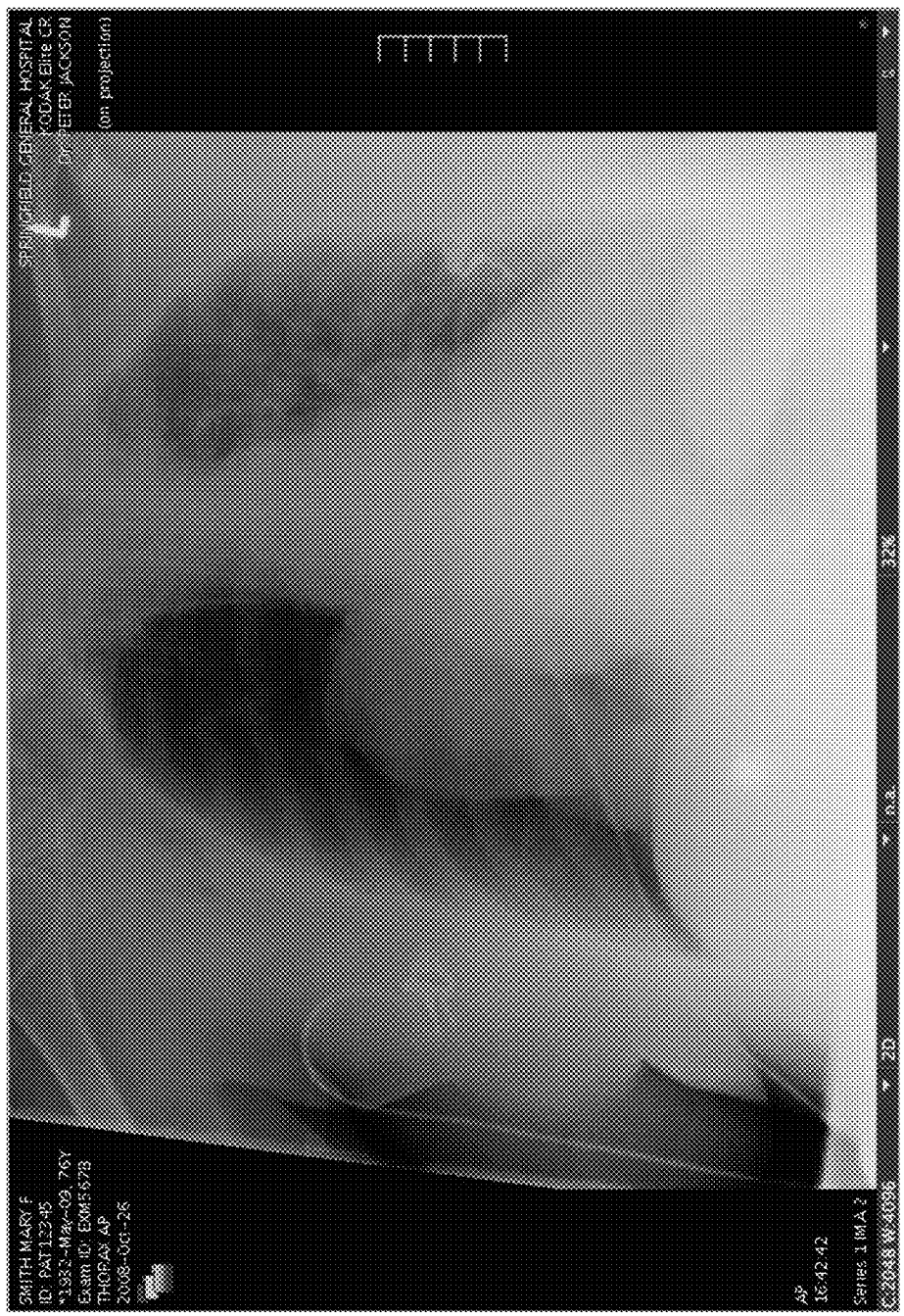
Figure 6:
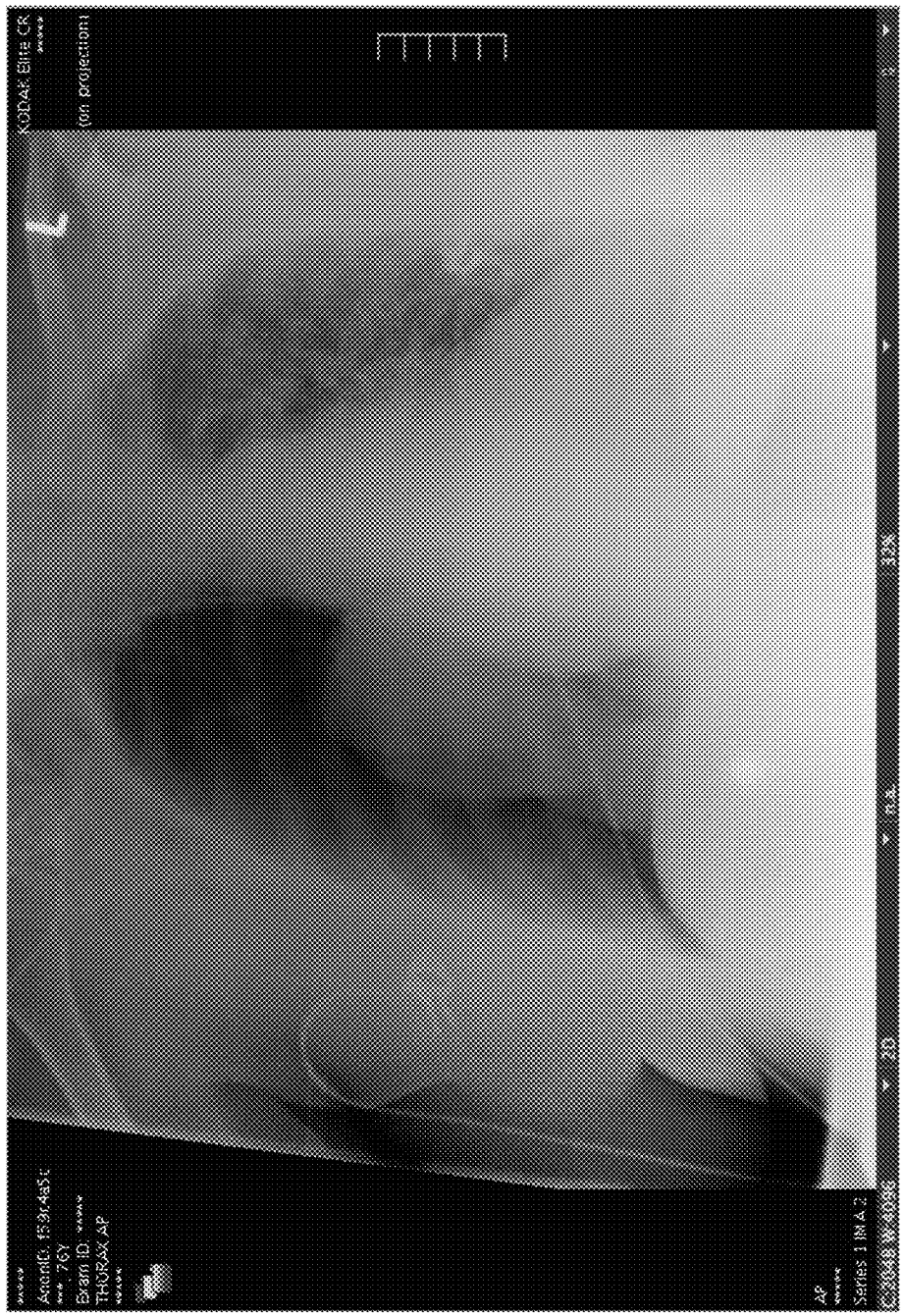
Figure 7A:
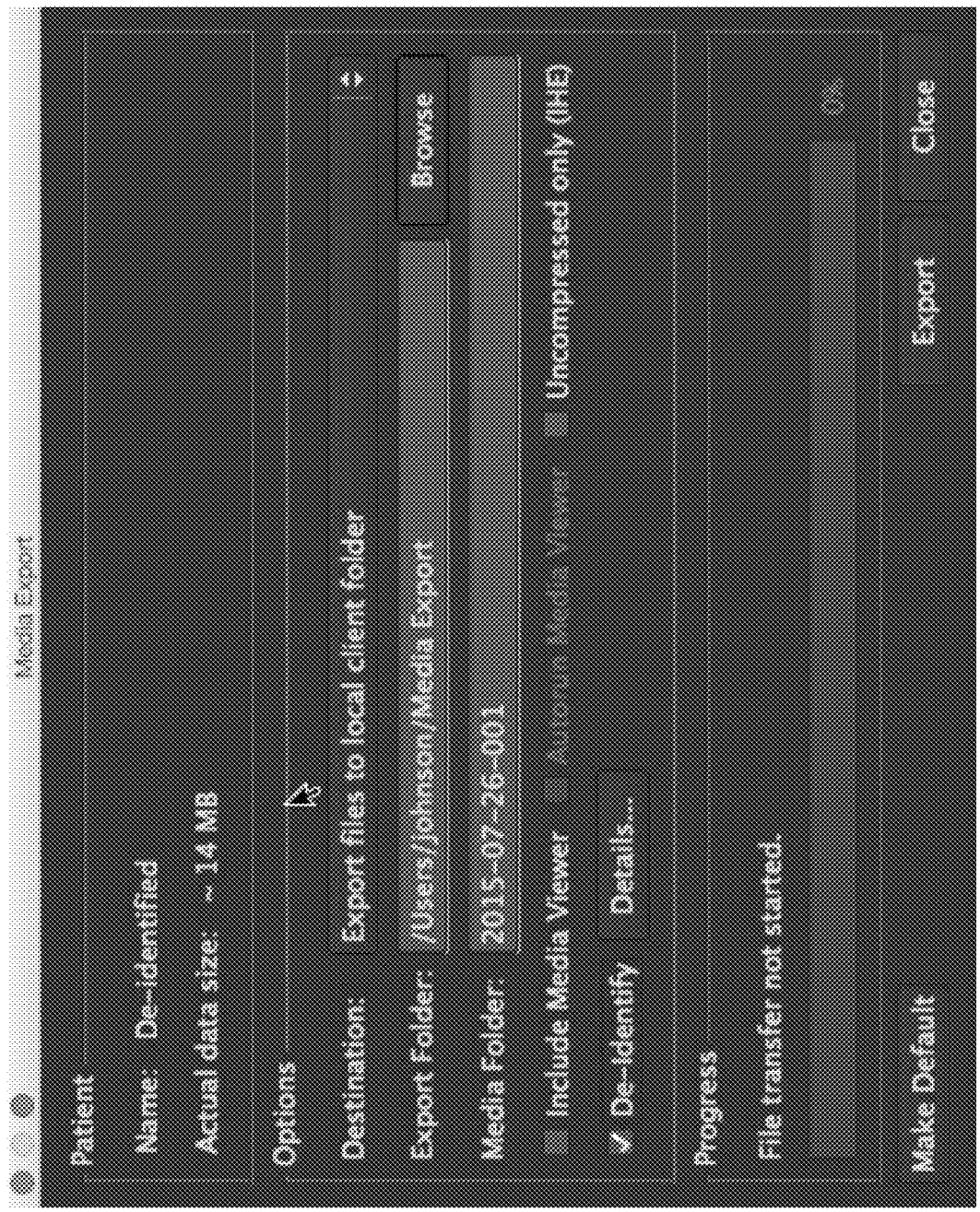
Figure 7B:
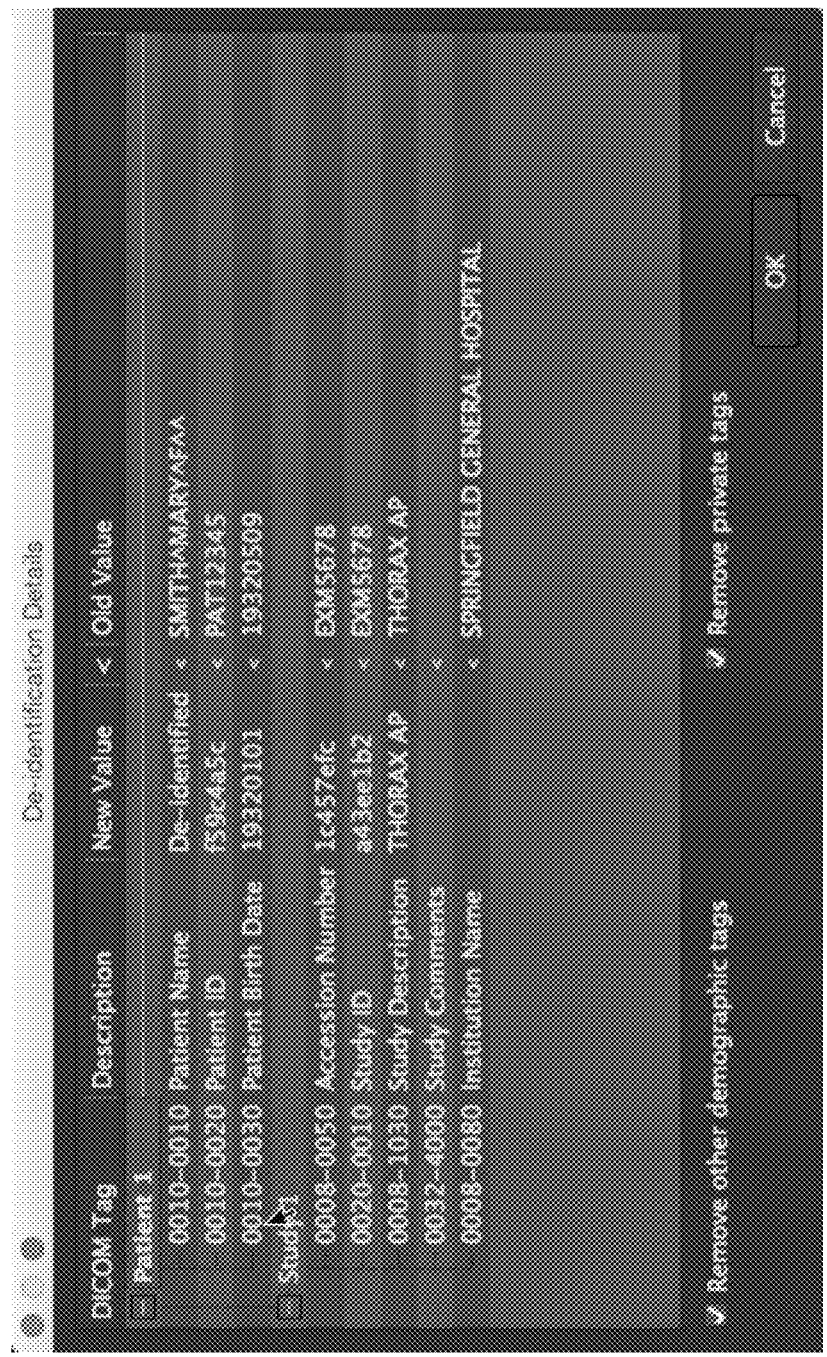
Figure 8:
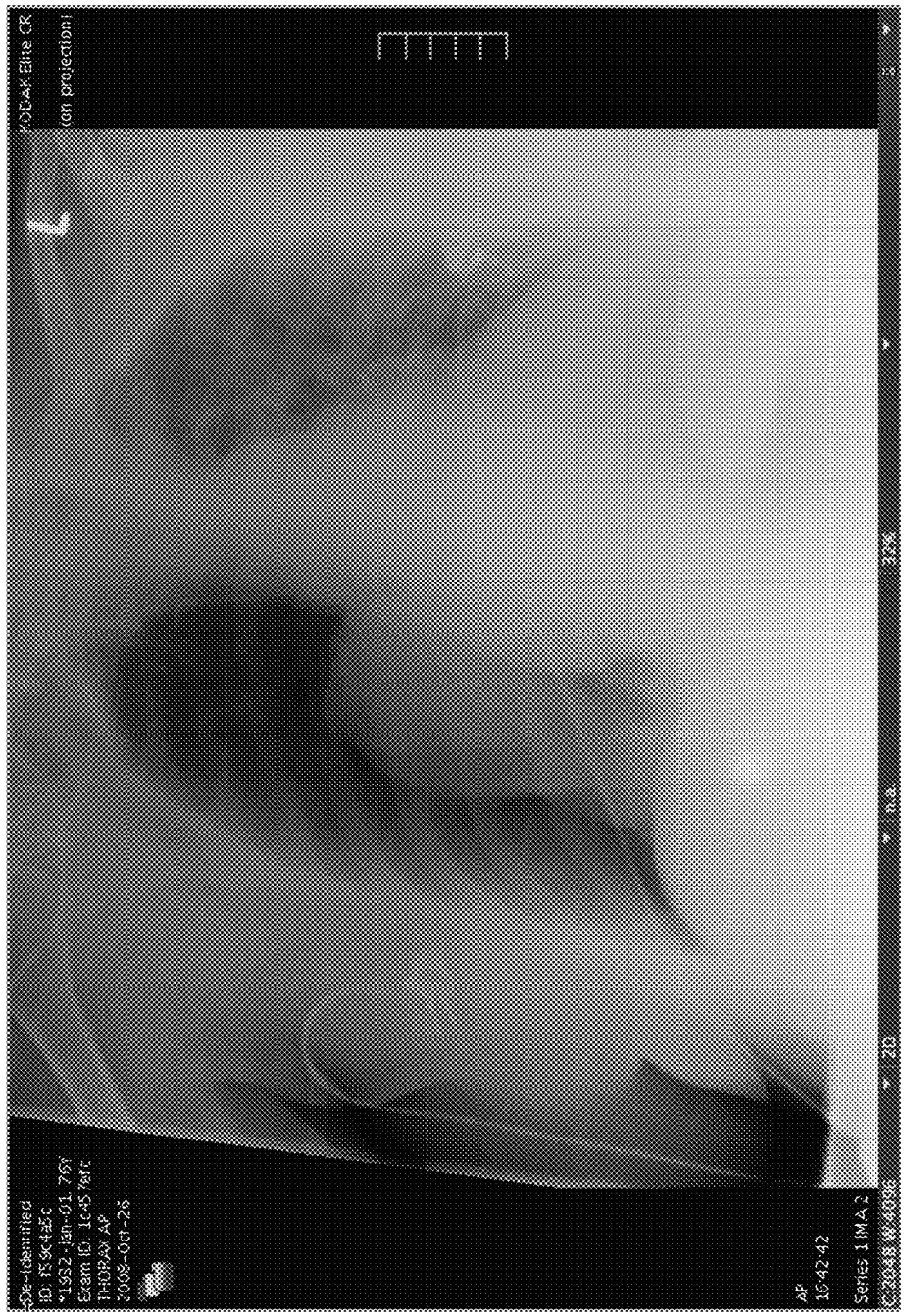

FIG. 3A shows an artist's impression of a dialog for exporting an exam. The dialog offers a De-Identification option. Clicking the Details button allows to configure the De-Identification. FIG. 3B shows an artist's impression of the dialog to configure the De-Identification details. Default values are filled in, depending on the system configuration. Note that in various embodiments of the invention, the fields that are affected by the anonymization may vary from system to system based on the exact use-case, the jurisdiction, changes in the Health Insurance Portability and Accountability Act (HIPAA), changes in other laws effecting the HIPAA regulations or other parameters. Accordingly, in various embodiments of the invention, the list can be configurable. In an embodiment of the invention, the ability to configure the list is password protected. In an embodiment of the invention, the ability to configure the list is password protected based on a security clearance. In various embodiments of the invention, a user with insufficient security clearance based on their user ID does not view the list as configurable. Note that in the configuration underlying FIG. 3B, the Study-Date and Study-Time Field are not affected by anonymization, while in the teaching mode configuration for FIG. 2 the Study-Date and Study-Time Field are anonymized. In various embodiments of the invention, these values can be overridden by a user with sufficient security clearance based on their user ID with either the original (un-anonymized values) or free-typed values. In the example configuration shown in FIG. 3B, the Patient ID field is pre-filled with the mapped patient ID as described herein. The accession number and study are pre-filled with unique random values. The Institution Name and Study Comment fields are left blank. FIG. 4 shows an artist's impression of a DICOM viewer displaying the images that were exported using the anonymization settings shown in FIG. 3B. In FIG. 4, the darkness of the DICOM viewer image is indicated using a grey scale shading system where 105 is white, black is black and the values 110, 115, 120, 125, 130, 135 and 140 indicate shades of gray from lightest to darkest. On the top left in FIG. 4 the 'Patient Name' is replaced with the label De-identified, the 'Patient ID' is replaced with 'ID' which is f59c4a5c*1932-Jan-01.76Y, the 'Exam ID' is 1c457efc, the 'Study (Exam) Description' remains THORAX AP, and the 'Study Date' is 2008-Oct-26. On the top right, FIG. 4 does not show the 'Hospital Name', but still shows the 'Imaging Device Name' as KODAK Elite CR, and the 'Physician's Name' is omitted. Further, FIG. 4 shows on the lower left the 'Imaging Orientation' as AP, the 'Acquisition Time' is 16:42:42, and the 'Series/Image number' as 1 IMA 2. Note that in an embodiment of the invention, in a 'teaching mode' only the viewer displays the data with anonymized PII. In an alternative embodiment of the invention, the information in the files is permanently anonymized and the viewer does not have to be in the 'teaching mode' to insure that the PII is not disclosed.

This approach has three very important characteristics. (i) It generates the same mapped id, if the input is the same. This means that two images belonging to the same patient can be exported independently, and without storing the mapped ID, both images will have the same mapped ID. (ii) Secure Hash Algorithms are not reversible. This means that even if the algorithm and the fields that are used to build the mapped ID are known, the value of the fields cannot be derived from the mapped ID. Therefore no re-identification is possible. (iii) The first characteristic (see (i) above) is achieved without storing the mapped value.

In multi-institution scenarios, where each institution independently assigns identifiers, the identifier that is used for one patient in one organization might also be used for a different patient in another organization. If data from both organizations are pooled, e.g. for a scientific study, this might lead to wrong conclusions, as images from different patients might seemingly relate to the same patient in the anonymized data set, as their patient ID and hence their mapped patient id would be the same. For example a first hospital might use Patient ID 1234 for one patient, while a second hospital might use the same ID 1234 for a different patient.

The present invention overcomes this issue by computing an institution aware mapped id. In an embodiment of the present invention, the institution name, or another institution identifier is added to the list of input fields to the secure hash function. Examples of suitable identifiers are DICOM tags (0008,0080) or (0010,0021). In this way, the mapped ID will be different for two patients with the same ID coming from two different hospitals. Note, that the secure hash function is not reversible. This means that it is not possible to determine the original patient ID from the mapped ID, nor is it possible to even determine the originating institution or hospital from the mapped ID.

SHA-1 and similar secure hash function are designed for cryptographic use. Most use cases described above do not require the same cryptographic strength, as the aim is not some kind of encryption. In an embodiment of the present invention, a subset of the phi of the SHA-1 function instead of the full set of phi of the SHA-1 function can be used in order to make identifiers not overly long.

In an embodiment of the present invention, in order to simplify the workflow the present invention integrates the anonymization into the data processing system (e.g. RIS, Imaging Workflow Solution, or PACS). In an embodiment of the present invention, a user based on their user ID with the associated permissions launches a function inside the system in order to anonymize and export the currently loaded study or studies, or one or more studies identified by search criteria. The data from the studies that were identified is then anonymized on the system. In an embodiment of the present invention, the data from the studies that were identified is then anonymized on the server, and only then transmitted to another network device or stored to a hard disk or other media.

This has key advantages compared to first exporting and then anonymizing. Besides increased efficiency, it ensures that the PII never leaves the original system, which is particularly important in situations where the medical diagnosis report is to be used off-shore.

Another scenario is the demonstration of clinical cases inside the organization, i.e. without any data export, but where not everybody in the audience might be entitled to see the PII, e.g. a lecture for students. Instead of creating anonymized copies in this case, the present invention allows on-the-fly anonymization. This saves significant amounts of time in educational institutions, such as university hospitals.

In an embodiment of the present invention, a user based on their user ID can start the client application of the clinical software system in a dedicated presentation mode. In an alternative embodiment of the present invention, a user based on their user ID can turn on a presentation mode so that from that point onwards information displayed on the screen that contains PII is replaced with the mapped values.

Often, presentations are prepared by adding relevant cases to a worklist. However, it is also possible to open a case by typing in an original identifier, if the presenter has noted that in his or her preparatory notes. In an embodiment of the present invention, in the 'Anonymized Presentation Mode', any PII text fields used for searching will not display the actual characters typed in, but instead just show dots or other replacement characters. In this way the presenter can open relevant cases in front of the audience, e.g. using a video projector, without cumbersome preparatory work, and without disclosing PII. While a student viewing the presentation can make a notation of an output, that output has only value as confirming the output. That is, if after the presentation the student asks the presenter a question about that output, the notation cannot be used to retrieve the presentation. However, if the presenter retrieves the output (by typing in the appropriate input), the output when displayed will have the same notation, and thus confirm that this was the presentation to which the question related.

In an embodiment of the invention, a method for displaying medical diagnostic reports comprises the steps of receiving one or more medical diagnostic reports, retrieving one or more phi of metadata containing PHI and/or PII in the one or more medical diagnostic reports, computing one or more concatenated values for the one or more phi of metadata using a separator character, computing one or more secure values for the one or more concatenated values using a secure hash function and displaying the one or more medical diagnostic reports, where the secure value is substituted for each phi of the one or more phi of metadata.

In an embodiment of the invention, a method for exporting medical diagnostic reports comprises the steps of receiving a medical diagnostic report, retrieving a phi of protected health information (PII)j, for each j, where j is an integer between 1 and J, where J is the number of phi of PII, computing a concatenated value (Cj) for each PIIj, for each j, where j is an integer between 1 and J, computing a Mj, where Mj is given by SHA1(Cj), for each j, where SHA1 is the SHA-1 secure hash function and exporting the medical diagnostic report, where one or more Mj are substituted for one or more PIIj, for each j.

In an embodiment of the invention, a method for displaying medical diagnostic reports comprises the steps of receiving one or more medical diagnostic reports, retrieving one or more phi of metadata in the one or more medical diagnostic reports, computing one or more concatenated values for the one or more phi of metadata using a separator character, computing one or more secure values for the one or more concatenated values using a secure hash function and exporting the one or more medical diagnostic reports, where the one or more secure values are substituted for the one or more phi metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing protected health information in the one or more medical reports, computing a concatenated value for each of the one or more phi of metadata using a separator character, computing a secure value for each of the concatenated values using a secure hash function and exporting to the first client the one or more medical diagnostic reports, where the secure value is substituted for each phi of the one or more phi of metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing protected health information in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES and exporting to the first client the one or more medical diagnostic reports, where the secure value is substituted for each phi of the one or more phi of metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing protected health information in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES, where the secure hash function displayed cannot be reversed to generate the corresponding phi of metadata and exporting to the first client the one or more medical diagnostic reports, where the secure value is substituted for each phi of the one or more phi of metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing protected health information in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES, where the secure hash function displayed cannot be reversed to generate the corresponding phi of metadata, where the secure hash function displayed in a first medical report is the same as the secure hash function displayed in a second medical report when the corresponding phi of metadata in the first medical report is the same as the corresponding phi of metadata in the second medical report and exporting to the first client the one or more medical diagnostic reports, where the secure value is substituted for each phi of the one or more phi of metadata in the one or more exported medical diagnostic reports.

In an embodiment of the invention, a method for displaying medical diagnostic reports comprises the steps of receiving one or more medical reports, retrieving one or more phi of metadata containing protected health information in the one or more medical reports, computing a concatenated value for each of the one or more phi of metadata using a separator character, computing a secure value for each of the concatenated values using a secure hash function and displaying the one or more medical reports, where the secure value is substituted for each phi of the one or more phi of metadata.

In an embodiment of the invention, a method for displaying medical diagnostic reports comprises the steps of receiving one or more medical reports, retrieving one or more phi of metadata containing protected health information in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES and displaying the one or more medical reports, where the secure value is substituted for each phi of the one or more phi of metadata.

In an embodiment of the invention, a method for displaying medical diagnostic reports comprises the steps of receiving one or more medical reports, retrieving one or more phi of metadata containing protected health information in the one or more medical reports, computing a concatenated value for each of the one or more phi of metadata using a separator character, computing a secure value for each of the concatenated values using a secure hash function and exporting the one or more medical reports, where the secure value is substituted for each phi of the one or more phi of metadata in the one or more exported medical reports.

In an embodiment of the invention, a method for displaying medical diagnostic reports comprises the steps of receiving one or more medical reports, retrieving one or more phi of metadata containing protected health information in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES and exporting the one or more medical reports, where the secure value is substituted for each phi of the one or more phi of metadata in the one or more exported medical reports.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and displaying the one or more medical reports, where the one or more secure values are substituted for the one or more phi of metadata.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function selected from the group consisting of MD4, MD5, SHA-1, SHA-2, Skein, and BLAKE and displaying the one or more medical reports, where the one or more secure values are substituted for the one or more phi of metadata.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and displaying the one or more medical reports, where the one or more secure values are substituted for the one or more phi of metadata, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and displaying the one or more medical reports, where the one or more secure values are substituted for the one or more phi of metadata, where a first secure value displayed corresponding to a first phi of metadata in a first medical report is the same as a second secure value corresponding to a second phi of metadata displayed in a second medical report when the first phi of metadata is the same as the second phi of metadata, where when the first secure value displayed is the same as the second secure value does not rely on storing one or both the first secure value and the second secure value.

In an embodiment of the invention, a method that displays an anonymized medical report comprising the steps of receiving a medical report, retrieving one or more phi of protected health information (PIIj), where j is an integer between 1 and J, where J is the number of phi of PII in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J.

In an embodiment of the invention, a method that displays an anonymized medical report comprising the steps of receiving a medical report, retrieving one or more phi of protected health information (PIIj), where j is an integer between 1 and J, where J is the number of phi of PII in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, where in the displayed medical report the one or more Mj cannot be used to generate the one or more PIIj.

In an embodiment of the invention, a method that displays an anonymized medical report comprising the steps of receiving a medical report, retrieving one or more phi of protected health information (PIIj), where j is an integer between 1 and J, where J is the number of phi of PII in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, where a first Mj (j=1) displayed in a first medical report is the same as a second Mj (j=2) displayed in a second medical report when $PII_1$ in the first medical report is equal to $PII_2$ in the second medical report.

In an embodiment of the invention, a method that displays an anonymized medical report comprising the steps of receiving a medical report, retrieving one or more phi of protected health information (PIIj), where j is an integer between 1 and J, where J is the number of phi of PII in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, where a first Mj (j=1) displayed in a first medical report is the same as a second Mj (j=2) displayed in a second medical report when $PII_1$ in the first medical report is equal to $PII_2$ in the second medical report, where when displaying two medical reports $M_1$ in a first medical report is equal to $M_2$ in a second medical report does not rely on storing one or both $M_1$ and $M_2$.

In an embodiment of the invention, a method that displays an anonymized medical report comprising the steps of receiving a medical report, retrieving one or more phi of protected health information (PIIj), where j is an integer between 1 and J, where J is the number of phi of PII in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, further comprising using a separator character between each Mj, where the separator character is not a value present in the one or more PIIj, where j is an integer between 1 and J.

In an embodiment of the invention, a method for exporting medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and exporting the one or more medical reports, where the one or more secure values are substituted for the one or more phi of metadata.

In an embodiment of the invention, a method for anonymization of medical reports comprising the steps of receiving one or more medical reports, retrieving one or more phi of metadata in the one or more medical reports, computing one or more concatenated values for the one or more phi of metadata, computing one or more secure values for the one or more concatenated values using a secure hash function and substituting the one or more secure values for the one or more phi of metadata in the medical reports.

In an embodiment of the invention, a method for anonymization of medical reports comprising the steps of receiving one or more medical reports, retrieving one or more phi of metadata containing protected health information in the one or more medical reports, computing one or more secure values for the one or more phi of metadata using a secure hash function and substituting the one or more secure values for the one or more phi of metadata.

In an embodiment of the invention, a method for anonymization of medical reports comprising the steps of receiving one or more medical reports, retrieving one or more phi of metadata containing protected health information in the one or more medical reports, adding an institution aware ID to the one or more phi of metadata, computing one or more concatenated values for the one or more phi of metadata, computing one or more secure values for the one or more concatenated values using a secure hash function and anonymizing the one or more medical reports, where the one or more secure hash functions are substituted for the one or more phi of metadata.

In an embodiment of the invention, a method for anonymization of medical reports comprising the steps of receiving one or more medical reports, retrieving one or more phi of metadata containing protected health information in the one or more medical reports, adding an institution aware ID to the one or more phi of metadata, computing one or more concatenated values for the one or more phi of metadata, computing one or more secure values for the one or more concatenated values using a secure hash function selected from the group consisting of MD4, MD5, SHA-1, SHA-2, Skein, BLAKE and AES and anonymizing the one or more medical reports, where the one or more secure hash functions are substituted for the one or more phi of metadata.

In an embodiment of the invention, a method for anonymization of medical reports comprising the steps of receiving one or more medical reports, retrieving one or more phi of metadata containing protected health information in the one or more medical reports, generating one or more combined values by adding an institution aware ID to the one or more phi of metadata, computing one or more secure values for the one or more combined values using a secure hash function and anonymizing the one or more medical reports, where the one or more secure values are substituted for the one or more phi of metadata.

In an embodiment of the invention, a method for anonymization of medical reports comprising the steps of receiving one or more medical reports, retrieving one or more phi of metadata containing protected health information in the one or more medical reports, generating one or more combined values by adding an institution aware ID to the one or more phi of metadata, computing one or more secure values for the one or more combined values using a secure hash function selected from the group consisting of MD4, MD5, SHA-1, SHA-2, Skein, BLAKE and AES and anonymizing the one or more medical reports, where the one or more secure values are substituted for the one or more phi of metadata.

In an embodiment of the invention, a method for anonymization of medical reports comprising the steps of receiving one or more medical reports, retrieving one or more phi of metadata containing protected health information in the one or more medical reports, generating one or more combined values by adding an institution aware ID to the one or more phi of metadata, concatenating the one or more phi of metadata prior to adding an institution aware ID, computing one or more secure values for the one or more combined values using a secure hash function and anonymizing the one or more medical reports, where the one or more secure values are substituted for the one or more phi of metadata.

In an embodiment of the invention, a method that displays an anonymized medical report comprising the steps of receiving a medical report, retrieving one or more phi of protected health information $(PII)j$, where $j$ is an integer between 1 and $J$, where $J$ is the number of phi of PII, computing a concatenated value $(Cj)$ for each $PIIj$, where $j$ is an integer between 1 and $J$, computing one or more $Mj$, where $Mj$ is given by $SF(Cj)$, where $j$ is an integer between 1 and $J$, where SF is a secure hash function and displaying the medical report, where one or more $Mj$ is substituted for each $PIIj$.

In an embodiment of the invention, a method that displays an anonymized medical report comprising the steps of receiving a medical report, retrieving one or more phi of protected health information $(PII)j$, where $j$ is an integer between 1 and $J$, where $J$ is the number of phi of PII, computing a concatenated value $(Cj)$ for each $PIIj$, where $j$ is an integer between 1 and $J$, computing one or more $Mj$, where $Mj$ is given by $SF(Cj)$, where $j$ is an integer between 1 and $J$, where SF is a secure hash function selected from the group consisting of MD4, MD5, SHA-1, SHA-2, Skein, BLAKE and AES and displaying the medical report, where one or more $Mj$ is substituted for each $PIIj$.

In an embodiment of the invention, a method comprises accessing one or more medical diagnostic reports, retrieving one or more phi of metadata containing protected health information in the one or more medical diagnostic reports, storing the one or more phi of metadata, adding an institution aware ID to the one or more phi of metadata to generate one or more combined values, concatenating the one or more combined values with a separator character to generate one or more concatenated values, computing one or more secure values from the one or more concatenated values, overwriting the one or more phi of metadata with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing protected health information in the one or more medical diagnostic reports, storing the one or more phi of metadata, adding an institution aware ID to the one or more phi of metadata to generate one or more combined values, concatenating the one or more combined values with a separator character to generate one or more concatenated values, computing one or more secure values from the one or more concatenated values using a secure hash function, overwriting the one or more phi of metadata with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing protected health information in the one or more medical diagnostic reports, storing the one or more phi of metadata, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, overwriting the one or more phi of metadata with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing protected health information in the one or more medical diagnostic reports, storing the one or more phi of metadata in a volatile computer memory location, adding an institution aware ID to the one or more phi of metadata to generate one or more combined values, concatenating the one or more combined values with a separator character to generate one or more concatenated values, computing one or more secure values from the one or more concatenated values, overwriting the one or more phi of metadata in the volatile computer memory location with the one or more secure values and displaying on a visual monitor the one or more medical diagnostic reports, where the one or more secure values are substituted for the one or more phi of metadata, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a method comprises accessing one or more medical diagnostic reports, retrieving one or more phi of metadata containing protected health information in the one or more medical diagnostic reports, storing the one or more phi of metadata in a volatile computer memory location, adding an institution aware ID to the one or more phi of metadata to generate one or more combined values, concatenating the one or more combined values with a separator character to generate one or more concatenated values, computing one or more secure values from the one or more concatenated values, overwriting the one or more phi of metadata in the volatile computer memory location with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing protected health information in the one or more medical diagnostic reports, storing the one or more phi of metadata, adding an institution aware ID to the one or more phi of metadata to generate one or more combined values, concatenating the one or more combined values with a backslash character to generate one or more concatenated values, computing one or more secure values from the one or more concatenated values, overwriting the one or more phi of metadata with the one or more secure values and displaying on a visual monitor the one or more medical diagnostic reports, where the one or more secure values are substituted for the one or more phi of metadata In an embodiment of the invention, a method comprises accessing one or more medical diagnostic reports, retrieving one or more phi of metadata containing protected health information in the one or more medical diagnostic reports, storing the one or more phi of metadata, adding an institution aware ID to the one or more phi of metadata to generate one or more combined values, where the institution aware ID is a DICOM tag (00zz,00xx) where zz and xx are integers between 1 and 99 selected to unambiguously identify the institution from one or more other institutions, concatenating the one or more combined values with a separator character to generate one or more concatenated values, computing one or more secure values from the one or more concatenated values, overwriting the one or more phi of metadata with the one or more secure values and displaying on a visual monitor the one or more medical diagnostic reports, where the one or more secure values are substituted for the one or more phi of metadata.

In an alternative embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function, generating one or more first amended medical diagnostic reports, where in the one or more medical diagnostic reports one or more of the one or more phi of metadata are overwritten with one or more secure values and exporting to the first client digital data processor the one or more first amended medical diagnostic reports.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, generating one or more first amended medical diagnostic reports, where in the one or more medical diagnostic reports one or more of the one or more phi of metadata are overwritten with one or more secure values and exporting to the first client digital data processor the one or more first amended medical diagnostic reports.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where one or both the one or more phi of metadata and the one or more secure values are stored in a volatile memory location.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a backslash character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where the institution aware ID is a DICOM tag (00zz,00xx) where zz and xx are integers between 1 and 99 selected to unambiguously identify an institution from one or more institutions.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where the one or more secure values cannot be used to generate the one or more phi of metadata.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where the system is adapted to receive instructions from the first client digital data processor to generate one or more second amended medical diagnostic reports, where in the one or more medical diagnostic reports all of the one or more phi of metadata are overwritten with one or more secure values and export to a second client digital data processor the one or more second amended medical diagnostic reports.

In another embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing protected health information in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more amended medical diagnostic reports, where the one or more phi of metadata in the one or more medical diagnostic reports are overwritten with one or more secure values and displaying the one or more amended medical diagnostic reports.

In an embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing protected health information in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function, generating one or more amended medical diagnostic reports, where the one or more phi of metadata in the one or more medical diagnostic reports are overwritten with one or more secure values and displaying the one or more amended medical diagnostic reports.

In an embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing protected health information in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, generating one or more amended medical diagnostic reports, where the one or more phi of metadata in the one or more medical diagnostic reports are overwritten with one or more secure values and displaying the one or more amended medical diagnostic reports In an embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing protected health information in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more amended medical diagnostic reports, where the one or more phi of metadata in the one or more medical diagnostic reports are overwritten with one or more secure values and displaying the one or more amended medical diagnostic report, where a first secure value displayed in the one or more amended medical diagnostic reports corresponding to a first phi of metadata in a first medical report is the same as a second secure value corresponding to a second phi of metadata displayed in a second medical report when the first phi of metadata is the same as the second phi of metadata.

In an embodiment of the invention, a non-transitory computer readable physical storage medium comprising a set of computer-readable instructions stored thereon which, when executed by a processing system, cause the processing system to retrieve one or more phi of metadata containing protected health information in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values, generate one or more amended medical diagnostic reports, where the one or more phi of metadata in the one or more medical diagnostic reports are overwritten with one or more secure values and display the one or more amended medical diagnostic reports.

In an embodiment of the invention, a non-transitory computer readable physical storage medium comprising a set of computer-readable instructions stored thereon which, when executed by a processing system, cause the processing system to retrieve one or more phi of metadata containing protected health information in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values using a secure hash function, generate one or more amended medical diagnostic reports, where the one or more phi of metadata in the one or more medical diagnostic reports are overwritten with one or more secure values and display the one or more amended medical diagnostic reports.

In an embodiment of the invention, a non-transitory computer readable physical storage medium comprising a set of computer-readable instructions stored thereon which, when executed by a processing system, cause the processing system to retrieve one or more phi of metadata containing protected health information in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values using a secure hash function selected from the group consisting of MD4, MD5, SHA-1, SHA-2, Skein, and BLAKE, generate one or more amended medical diagnostic reports, where the one or more phi of metadata in the one or more medical diagnostic reports are overwritten with one or more secure values and display the one or more amended medical diagnostic reports.

In an embodiment of the invention, a non-transitory computer readable physical storage medium comprising a set of computer-readable instructions stored thereon which, when executed by a processing system, cause the processing system to retrieve one or more phi of metadata containing protected health information in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values, generate one or more amended medical diagnostic reports, where the one or more phi of metadata in the one or more medical diagnostic reports are overwritten with one or more secure values and display the one or more amended medical diagnostic reports, where a first secure value displayed in the one or more amended medical diagnostic reports corresponding to a first phi of metadata in a first medical report is the same as a second secure value corresponding to a second phi of metadata displayed in a second medical report when the first phi of metadata is the same as the second phi of metadata.

In a different embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic report, where one or both the one or more phi of metadata and the one or more secure values are stored in a volatile memory location.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a backslash character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports, where the institution aware ID is a DICOM tag (00zz,00xx) where zz and xx are integers between 1 and 99 selected to unambiguously identify an institution from one or more institutions.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports, where the one or more secure values cannot be used to generate the one or more phi of metadata.

In an embodiment of the present invention, a method comprises providing a server computer including a graphics processing unit and a first memory, where the first memory stores a plurality of medical diagnostic reports, where the server computer, receiving a patient ID from a remote computer, where the patient ID identifies a patient at one or more institutions, where the remote computer includes a graphics processing unit and a second memory, locates in the first memory a medical diagnostic report based on the patient ID, where the medical diagnostic report includes a 3-D volumetric image reconstructed from a plurality of measured 2-D projection images and one or more phi of metadata containing protected health information, adds an institution aware ID to the one or more phi of metadata to generate one or more combined values, concatenates the one or more combined values with a separator character to generate one or more concatenated values, computes one or more secure values from the one or more concatenated values, where the one or more secure values are substituted for the one or more phi of metadata thereby producing an anonymized medical diagnostic report, computes three or more generated 2-D projection images based on three or more viewing directions ($\theta$), where a first viewing direction generated by a first straight line drawn between a first position and an object is used to compute a first generated 2-D projection image, where the angle between the first straight line and the first viewing direction is given by $\theta_0$, where $\theta_0$ is equal to zero, a second viewing direction generated by a second straight line drawn between a second position and the object is used to compute a second generated 2-D projection image, where the angle between the second straight line and the first straight line is given by $\theta_1$, and at least a third viewing direction generated by a third straight line drawn between a third position and the object is used to compute a third generated 2-D projection image, where the angle between the third straight line and the first straight line is $\theta_2$ and sends the anonymized medical diagnostic report including the three or more generated 2-D projection images and viewing instructions to a remote device which includes a graphics display unit and a second memory, where the remote computer stores the anonymized medical diagnostic report in the second memory, where display of the image stored in the second memory, where the viewing instructions determine that the three or more generated 2-D projection images are displayed on the graphics display unit in time delay corresponding with increasing $\theta$.

In an embodiment of the present invention, a method comprises providing a host computer, the host computer receiving a user ID and a patient ID from a remote computer, where the patient ID identifies a patient at one or more institutions, the host computer receiving a medical diagnostic report based on one or both the user ID and the patient ID, where the medical diagnostic report includes an image and one or more phi of metadata containing protected health information, the host computer adding an institution aware ID to the one or more phi of metadata to generate one or more combined values, the host computer concatenating the one or more combined values with a separator character to generate one or more concatenated values, the host computer computing one or more secure values from the one or more concatenated values, where the one or more secure values are substituted for the one or more phi of metadata thereby producing an anonymized medical diagnostic report and sending the anonymized medical diagnostic report to the remote computer.

In an embodiment of the present invention, a method comprises providing a host computer with a first memory which contains a plurality of medical diagnostic reports, the host computer receiving a user ID and a patient ID from a remote computer which includes a graphics processing unit and a second memory, the host computer retrieving a medical diagnostic report based on one or both the user ID and the patient ID, where the medical diagnostic report includes an image and one or more phi of metadata containing protected health information, the host computer adding an institution aware ID to the one or more phi of metadata to generate one or more combined values, the host computer concatenating the one or more combined values with a separator character to generate one or more concatenated values, the host computer computing one or more secure values from the one or more concatenated values, generating one or more first amended medical diagnostic reports, where the one or more phi of metadata are replaced with the one or more secure values and displaying on the remote computer the one or more first amended medical diagnostic reports.

In an embodiment of the invention, a method comprises retrieving one or more phi of metadata containing protected health information in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports and one or more second amended medical diagnostic reports, where in the one or more medical diagnostic reports one or more of the one or more phi of metadata are overwritten with the one or more secure values to generate the one or more first amended medical diagnostic reports and all of the one or more phi of metadata are overwritten with the one or more secure values to generate the one or more second amended medical diagnostic report, where the one or more phi of metadata are overwritten with the one or more secure values and exporting to the first client digital data processor the one or more first amended medical diagnostic reports and exporting to the second digital data processor the one or more second amended medical diagnostic reports.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents. The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

What is claimed:

1. A method of sending anonymized medical diagnostic reports to a remote device comprising:
   providing a host computer comprising a first memory on which is stored a plurality of medical diagnostic reports, the host computer:
   a) receiving a user ID and a patient ID from the remote device, where the patient ID identifies a patient at one or more institutions;
   b) receiving a dialog comprising a selectable option, where the selectable option is configured based on the user ID;
   c) interpreting the selectable option as an instruction to de-identify Patient Identifiable Information (PII);
   d) locating in the first memory a medical diagnostic report containing PII based on the patient ID, where the medical diagnostic report comprises:
      two or more images;
      one or more image series comprising an image set generated according to one or more image set rules;
      one or more first metadata containing PII associated with the two or more images; and
      one or more second metadata containing PII associated with the image set, where the one or more first metadata containing PII are not equal to the one or more second metadata containing PII;
   e) computing two or more secure values corresponding to the one or more first metadata containing PII and the one or more second metadata containing PII;
   f) substituting the two or more secure values for the one or more first metadata containing PII and the one or more second metadata containing PII;
   g) generating an anonymized medical diagnostic report comprising:
      the two or more images;
      the one or more image series; and
      the two or more secure values; and
   h) sending the anonymized medical diagnostic report to the remote device.

2. The method of claim 1, where the dialog is for exporting an exam.

3. The method of claim 2, where the dialog comprises one or more boxes, where a first box of the one or more boxes is the selectable option.

4. The method of claim 2, where configuring the selectable option triggers the substituting of the two or more secure values for the one or more first metadata containing PII and the one or more second metadata containing PII in step f).

5. The method of claim 1, where the two or more secure values are computed from one or more concatenated values using a secure hash function.

6. The method of claim 5, where the secure hash function is selected from the group consisting of MD4, MD5, SHA-1, SHA-2, Skein, and BLAKE.

7. The method of claim 1, further comprising adding a separator character to generate the two or more secure values.

8. The method of claim 1, further comprising adding an institution aware ID to generate each of the two or more secure values, where the institution aware ID is a code used to distinguish a first secure value of a first patient at a first institution from a second secure value of the first patient at a second institution.

9. The method of claim 8, where the institution aware ID has the form of a DICOM tag (00zz,00xx) where zz and xx are integers between 1 and 99.

10. The method of claim 8, where the institution aware ID is selected to unambiguously identify an institution from the one or more institutions.

11. The method of claim 1, where the two or more secure values are sent to a volatile memory location on the remote device.

12. A method to anonymize Patient Identifiable Information (PII) comprising:
   providing a host computer adapted to access a plurality of medical diagnostic reports, the host computer:
   a) receiving a user ID and a patient ID from a remote device, where the patient ID identifies a patient at one or more institutions, where the host computer receives a dialog comprising a selectable option, where the selectable option instructs the host computer to de-identify PII, where the selectable option is configured based on the user ID, where the host computer is configured to allow a teaching mode and a presentation mode, where the teaching mode is configured based on the user ID;
   b) locating in a first memory a medical diagnostic report containing PII based on the patient ID, where the medical diagnostic report comprises:
      two or more images;
      one or more image series comprising an image set generated according to one or more image set rules
      one or more first metadata containing PII associated with the two or more images; and
      one or more second metadata containing PII associated with the image set, where the one or more first metadata containing PII are not equal to the one or more second metadata containing PII;
   c) computing two or more secure values;
   d) substituting the two or more secure values for the one or more first metadata containing PII, where the teaching mode requires that a study date that forms part of either the one or more first metadata containing PII, and the one or more second metadata containing PII is anonymized, where the presentation mode does not require that the study date that forms part of either the one or more first metadata containing PII, and the one or more second metadata containing PII is anonymized, where the teaching mode requires that a study time that forms part of either the one or more first metadata containing PII, and the one or more second metadata containing PII is anonymized, where the presentation mode does not require that the study time that forms part of either the one or more first metadata containing PII, and the one or more second metadata containing PII is anonymized thereby producing an amended medical diagnostic report; and
   d) sending the amended medical diagnostic report with the two or more secure values to the remote device.

13. The method of claim 12, where the dialog is for exporting an exam.

14. The method of claim 12, where the dialog comprises one or more boxes, where a first box of the one or more boxes is the selectable option.

15. The method of claim 12, where configuring the selectable option triggers the substituting of the two or more secure values for the one or more first of metadata containing PII, and the one or more second metadata containing PII according to step d).

16. The method of claim 12, where the two or more secure values are computed from two or more concatenated values using a secure hash function.

17. The method of claim 16, where the secure hash function is selected from the group consisting of MD4, MD5, SHA-1, SHA-2, Skein, and BLAKE.

18. The method of claim 12, further comprising adding a separator character to generate the two or more secure values.

* * * * *